(12) United States Patent
Araki et al.

(10) Patent No.: US 9,316,588 B2
(45) Date of Patent: Apr. 19, 2016

(54) BIOASSAY METHOD FOR DETECTING PHYSIOLOGICALLY ACTIVE SUBSTANCE

(75) Inventors: Naohiro Araki, Osaka (JP); Mitsuru Iida, Osaka (JP); Kiyotaka Machida, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/997,489

(22) PCT Filed: Dec. 22, 2011

(86) PCT No.: PCT/JP2011/079806
§ 371 (c)(1),
(2), (4) Date: Jun. 24, 2013

(87) PCT Pub. No.: WO2012/086756
PCT Pub. Date: Jun. 28, 2012

(65) Prior Publication Data
US 2013/0280734 A1  Oct. 24, 2013

(30) Foreign Application Priority Data
Dec. 24, 2010  (JP) .................................. 2010-288305

(51) Int. Cl.
G01N 21/64  (2006.01)
G01N 33/68  (2006.01)

(52) U.S. Cl.
CPC ........ *G01N 21/6486* (2013.01); *G01N 33/6872* (2013.01); *G01N 2333/726* (2013.01); *G01N 2500/10* (2013.01); *G01N 2800/042* (2013.01)

(58) Field of Classification Search
None
See application file for complete search history.

(56) References Cited

U.S. PATENT DOCUMENTS

| | | |
|---|---|---|
| 2004/0171005 A1 | 9/2004 | Printen et al. |
| 2006/0073468 A1 | 4/2006 | Korschen et al. |
| 2007/0031834 A1 | 2/2007 | Wunder |
| 2007/0065818 A1 | 3/2007 | Foti et al. |
| 2009/0104644 A1 | 4/2009 | Korschen et al. |
| 2010/0159449 A1 | 6/2010 | Iida et al. |
| 2012/0149036 A1 | 6/2012 | Araki |

FOREIGN PATENT DOCUMENTS

| | | |
|---|---|---|
| CN | 1761879 A | 4/2006 |
| JP | 2005/506053 | 3/2005 |
| JP | 2005-507245 | 3/2005 |
| WO | WO2005/041758 A2 | 5/2005 |
| WO | WO 2007/139080 | 6/2007 |
| WO | WO2007/100618 A2 | 9/2007 |
| WO | WO 2008/123901 | 10/2008 |
| WO | WO 2011/001885 A1 | 1/2011 |

OTHER PUBLICATIONS

Chou et al, Regulation of aquaporin-2 trafficking by vasopressin in the renal collecting duct. Roles of ryanodine-sensitive Ca2+ stores and calmodulin. J. Biol. Chem. 275:36839-36846, 2000.*
Extended European Search Report for EP Application No. 11850746. 6, dated Apr. 28, 2014, 7 pages.
Tang, Yi et al., "Real-Time and High Throughput Monitoring of cAMP in Live Cells Using a Fluorescent Membrane Potential-Sensitive Dye," *Assay and Drug Development Technologies*, vol. 4, No. 4, pp. 461-471, Aug. 2006.
Seibold, Anita et al., "Structure and Chromosomal Localization of the Human Antidiuretic Hormone Receptor Gene," Am. J. Hum. Genet., 1992, vol. 51, pp. 1078-1083.
Graziano, Michael P. et al., "Cloning and Functional Expression of a Human Glucagon-Like Peptide-1 Receptor," Biochemical and Biophysical Research Communications, Oct. 15, 1993, pp. 141-146, vol. 196, No. 1.
Inoue, H. et al., "Aequorea Victoria mRNA for Apoaequorin, Clone:UTAEQ04," Mar. 1, 2006, 1 page, Database DDBJ/EMBL/Genbank [online], Accession No. AB103337, http://www.ncbi.nim.nih.gov/nuccore/AB103337 retrieved on Feb. 14, 2012.
Japanese Patent Office, "International Search Report," for International Application No. PCT/JP2011/079806, Feb. 15, 2012, 4 pages.
Robertson, Gary L. et al., "Development and Clinical Application of a New Method for the Radioimmunoassay of Arginine Vasopressin in Human Plasma," The Journal of Clinical Investigation, Sep. 1973, pp. 2340-2352., vol. 52.
Plosker, Greg L., "Tolvaptan," Drugs, 2010, pp. 443-454, vol. 70 (4).
Moritoh, Yusuke et al., "Chronic Administration of Alogliptin, a Novel, Potent, and Highly Selective Dipeptidyl Peptidase-4 Inhibitor, Improves Glycemic Control and Beta-Cell Function in Obese Diabetic ob/ob Mice," European Journal of Pharmacology 583, 2008, pp. 325-332.
Talukdar, Saswata et al., "Targeting GPR120 and Other Fatty Acid-Sensing GPCRs Ameliorates Insulin Resistance and Inflammatory Diseases," Trends in Pharmacological Sciences, Sep. 2011, pp. 543-550, vol. 32, No. 9.
Yabe, Daisuke et al., "Little Enhancement of Meal-Induced Glucagon-Like Peptide 1 Secretion in Japanese: Comparison of Type 2 Diabetes Patients and Healthy Controls," Journal of Diabetes Investigation, Feb./Apr. 2010, pp. 56-59, vol. 1, Issue 1/2.
Heijboer, Annemieke C. et al., "Analysis of Glucagon-Like Peptide 1: What to Measure?", Clinica Chimica Acta 412, 2011, pp. 1191-1194.
"Translation of the International Preliminary Report on Patentability and Written Opinion from the International Bureau," in International Application No. PCT/JP2011/079806, mailed Jul. 11, 2013.
First Office Action and Search Report for CN Application No. 201180062475.8 dated Jun. 11, 2014.

* cited by examiner

*Primary Examiner* — Ruixiang Li
(74) *Attorney, Agent, or Firm* — Finnegan, Henderson, Farabow, Garrett & Dunner, L.L.P.

(57) ABSTRACT

Provided are a procedurally simple and safe method and kit for measuring the concentration in a biological sample of a physiologically active substance which binds to a receptor that causes a change in intracellular cAMP concentration. By providing a composition including genetically-modified cells which show co-expression of a receptor that causes a change in intracellular cAMP concentration, a cyclic nucleotide-responsive calcium channel, and aequorin luminescent protein, it is possible to measure how much of a physiologically active substance which binds to said receptor is included in a biological sample.

13 Claims, 17 Drawing Sheets

SEQUENCE LISTING

<160> NUMBER OF SEQ ID NOS: 9

<210> SEQ ID NO 1
<211> LENGTH: 309
<212> TYPE: PRT
<213> ORGANISM: Human

<400> SEQUENCE: 1

```
Met Leu Met Ala Ser Thr Thr Ser Ala Val Pro Gly His Pro Ser Leu
1               5                   10                  15

Pro Ser Leu Pro Ser Asn Ser Ser Gln Glu Arg Pro Leu Asp Thr Arg
            20                  25                  30

Asp Pro Leu Leu Ala Arg Ala Glu Leu Ala Leu Leu Ser Ile Val Phe
        35                  40                  45

Val Ala Val Ala Leu Ser Asn Gly Leu Val Leu Ala Ala Leu Ala Arg
    50                  55                  60
```

```
Arg Gly Arg Arg Gly His Trp Ala Pro Ile His Val Phe Ile Gly His
 65                  70                  75                  80

Leu Cys Leu Ala Asp Leu Ala Val Ala Leu Phe Gln Val Leu Pro Gln
                 85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Tyr
        115                 120                 125

Met Ile Leu Ala Met Thr Leu Asp Arg His Arg Ala Ile Cys Arg Pro
    130                 135                 140

Met Leu Ala Tyr Arg His Gly Ser Gly Ala His Trp Asn Arg Pro Val
145                 150                 155                 160

Leu Val Ala Trp Ala Phe Ser Leu Leu Leu Ser Leu Pro Gln Leu Phe
                165                 170                 175

Ile Phe Ala Gln Arg Asn Val Glu Gly Ser Gly Val Thr Asp Cys
            180                 185                 190

Trp Ala Cys Phe Ala Glu Pro Trp Gly Arg Arg Thr Tyr Val Thr Trp
        195                 200                 205

Ile Ala Leu Met Val Phe Val Ala Pro Thr Leu Gly Ile Ala Ala Cys
    210                 215                 220

Gln Val Leu Ile Phe Arg Glu Ile His Ala Ser Leu Val Pro Gly Pro
225                 230                 235                 240

Ser Glu Arg Pro Gly Gly Arg Arg Gly Arg Arg Thr Gly Ser Pro
                245                 250                 255

Gly Glu Gly Ala His Val Ser Ala Val Ala Lys Thr Val Arg Met
            260                 265                 270

Thr Leu Val Ile Val Val Tyr Val Leu Cys Trp Ala Pro Phe Phe
        275                 280                 285

Leu Val Gln Leu Trp Ala Ala Trp Asp Pro Glu Ala Pro Leu Glu Gly
        290                 295                 300

Gly Cys Ser Arg Gly
305

<210> SEQ ID NO 2
<211> LENGTH: 664
<212> TYPE: PRT
<213> ORGANISM: Artificial
<220> FEATURE:
<223> OTHER INFORMATION: modified CNG alpha2

<400> SEQUENCE: 2

Met Met Thr Glu Lys Ser Asn Gly Val Lys Ser Pro Ala Asn Asn
1               5                   10                  15

His Asn His Pro Pro Pro Ser Ile Lys Ala Asn Gly Lys Asp Asp
            20                  25                  30

His Arg Ala Gly Ser Arg Pro Gln Ser Val Ala Ala Asp Asp Asp Thr
        35                  40                  45

Ser Ser Glu Leu Gln Arg Leu Ala Glu Met Asp Thr Pro Arg Arg Gly
    50                  55                  60

Arg Gly Gly Phe Arg Arg Ile Val Arg Leu Val Gly Ile Ile Arg Asp
 65                 70                  75                  80

Trp Ala Asn Lys Asn Phe Arg Glu Glu Pro Arg Pro Asp Ser Phe
                85                  90                  95

Leu Glu Arg Phe Arg Gly Pro Glu Leu Gln Thr Val Thr Thr His Gln
            100                 105                 110
```

-continued

```
Gly Asp Gly Lys Gly Asp Lys Asp Gly Glu Gly Lys Gly Thr Lys Lys
            115                 120                 125
Lys Phe Glu Leu Phe Val Leu Asp Pro Ala Gly Asp Trp Tyr Tyr Arg
130                 135                 140
Trp Leu Phe Val Ile Ala Met Pro Val Leu Tyr Asn Trp Cys Leu Leu
145                 150                 155                 160
Val Ala Arg Ala Cys Phe Ser Asp Leu Gln Arg Asn Tyr Phe Val Val
                165                 170                 175
Trp Leu Val Leu Asp Tyr Phe Ser Asp Thr Val Tyr Ile Ala Asp Leu
            180                 185                 190
Ile Ile Arg Leu Arg Thr Gly Phe Leu Glu Gln Gly Leu Leu Val Lys
        195                 200                 205
Asp Pro Lys Lys Leu Arg Asp Asn Tyr Ile His Thr Leu Gln Phe Lys
    210                 215                 220
Leu Asp Val Ala Ser Ile Ile Pro Thr Asp Leu Ile Tyr Phe Ala Val
225                 230                 235                 240
Gly Ile His Ser Pro Glu Val Arg Phe Asn Arg Leu Leu His Phe Ala
                245                 250                 255
Arg Met Phe Glu Phe Phe Asp Arg Thr Glu Thr Arg Thr Ser Tyr Pro
            260                 265                 270
Asn Ile Phe Arg Ile Ser Asn Leu Val Leu Tyr Ile Leu Val Ile Ile
        275                 280                 285
His Trp Asn Ala Cys Ile Tyr Tyr Ala Ile Ser Lys Ser Ile Gly Phe
    290                 295                 300
Gly Val Asp Thr Trp Val Tyr Pro Asn Ile Thr Asp Pro Glu Tyr Gly
305                 310                 315                 320
Tyr Leu Ala Arg Glu Tyr Ile Tyr Cys Leu Tyr Trp Ser Thr Leu Thr
                325                 330                 335
Leu Thr Thr Ile Gly Glu Thr Pro Pro Pro Val Lys Asp Glu Glu Tyr
            340                 345                 350
Leu Phe Val Ile Phe Asp Phe Leu Ile Gly Val Leu Ile Phe Ala Thr
        355                 360                 365
Ile Val Gly Asn Val Gly Ser Met Ile Ser Asn Met Asn Ala Thr Arg
    370                 375                 380
Ala Glu Phe Gln Ala Lys Ile Asp Ala Val Lys His Tyr Met Gln Phe
385                 390                 395                 400
Arg Lys Val Ser Lys Asp Met Glu Ala Lys Val Ile Lys Trp Phe Asp
                405                 410                 415
Tyr Leu Trp Thr Asn Lys Lys Thr Val Asp Glu Arg Glu Val Leu Lys
            420                 425                 430
Asn Leu Pro Ala Lys Leu Arg Ala Glu Ile Ala Ile Asn Val His Leu
        435                 440                 445
Ser Thr Leu Lys Lys Val Arg Ile Phe Gln Asp Trp Glu Ala Gly Leu
    450                 455                 460
Leu Val Glu Leu Val Leu Lys Leu Arg Pro Gln Val Phe Ser Pro Gly
465                 470                 475                 480
Asp Tyr Ile Cys Arg Lys Gly Asp Ile Gly Lys Glu Met Tyr Ile Ile
                485                 490                 495
Lys Glu Gly Lys Leu Ala Val Val Ala Asp Asp Gly Val Thr Gln Tyr
            500                 505                 510
Ala Leu Leu Ser Ala Gly Ser Cys Phe Gly Glu Ile Ser Ile Leu Asn
        515                 520                 525
Ile Lys Gly Ser Lys Met Gly Asn Arg Arg Thr Ala Asn Ile Arg Ser
```

```
            530                 535                 540
Leu Gly Tyr Ser Asp Leu Phe Cys Leu Ser Lys Asp Leu Met Glu
545                 550                 555                 560

Ala Val Thr Glu Tyr Pro Asp Ala Lys Lys Val Leu Glu Glu Arg Gly
                565                 570                 575

Arg Glu Ile Leu Met Lys Met Gly Leu Leu Asp Glu Asn Glu Val Ala
                580                 585                 590

Ala Ser Met Glu Val Asp Val Gln Gly Lys Leu Glu Gln Leu Glu Thr
            595                 600                 605

Asn Met Glu Thr Leu Tyr Thr Arg Phe Ala Arg Leu Leu Ala Glu Tyr
            610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Ala Val Ala Glu
                660

<210> SEQ ID NO 3
<211> LENGTH: 228
<212> TYPE: PRT
<213> ORGANISM: Artificial
<220> FEATURE:
<223> OTHER INFORMATION: modified aequorin

<400> SEQUENCE: 3

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Pro Pro Glu
                20                  25                  30

Gly Lys Leu Gly Ile Met Lys Val Lys Leu Thr Ser Asp Phe Asp Asn
            35                  40                  45

Pro Lys Trp Ile Gly Arg His Lys His Met Phe Asn Phe Leu Asp Val
        50                  55                  60

Asn His Asn Gly Arg Ile Ser Leu Asp Glu Met Val Tyr Lys Ala Ser
65                  70                  75                  80

Asp Ile Val Ile Asn Asn Leu Gly Ala Thr Pro Glu Gln Ala Lys Arg
                85                  90                  95

His Lys Asp Ala Val Glu Ala Phe Phe Gly Gly Ala Gly Met Lys Tyr
                100                 105                 110

Gly Val Glu Thr Glu Trp Pro Glu Tyr Ile Glu Gly Trp Lys Arg Leu
            115                 120                 125

Ala Thr Glu Glu Leu Glu Arg Tyr Ser Lys Asn Gln Ile Thr Leu Ile
        130                 135                 140

Arg Leu Trp Gly Asp Ala Leu Phe Asp Ile Ile Asp Lys Asp Gln Asn
145                 150                 155                 160

Gly Ala Ile Thr Leu Asp Glu Trp Lys Ala Tyr Thr Lys Ser Ala Gly
                165                 170                 175

Ile Ile Gln Ser Ser Glu Asp Cys Glu Glu Thr Phe Arg Val Cys Asp
                180                 185                 190

Ile Asp Glu Ser Gly Gln Leu Asp Val Asp Glu Met Thr Arg Gln His
            195                 200                 205

Leu Gly Phe Trp Tyr Thr Met Asp Pro Ala Cys Glu Lys Leu Tyr Gly
        210                 215                 220

Gly Ala Val Pro
```

<210> SEQ ID NO 4
<211> LENGTH: 1995
<212> TYPE: DNA
<213> ORGANISM: Mus musculus

<400> SEQUENCE: 4

| | | | | | |
|---|---|---|---|---|---|
| atgatgaccg | aaaaatccaa | cggtgtgaag | agctctccag | ctaataacca | taaccatcat | 60 |
| cctcctcctt | ctatcaaggc | caatggcaaa | gatgaccaca | gggcaggtag | cagaccacag | 120 |
| tctgtggcag | ctgatgatga | cacttcctca | gaactgcaaa | ggttggcaga | gatggatact | 180 |
| ccacgcaggg | gaagggtgg | cttccgaagg | attgtccgcc | tggtgggat | catcagagac | 240 |
| tgggccaaca | aaaatttccg | tgaggaggaa | ccaagacctg | actccttcct | agagcgtttc | 300 |
| cgtgggcctg | agctccagac | tgtgacaacc | catcagggg | atggcaaagg | cgacaaggac | 360 |
| ggcgagggaa | agggcaccaa | aaagaaattt | gaactgtttg | ttttggaccc | agctggagac | 420 |
| tggtattacc | gttggttgtt | tgtcattgcc | atgcctgttc | tttacaactg | gtgtctgttg | 480 |
| gtagccagag | cctgcttcag | tgatctacag | agaaactatt | ttgtggtatg | gctggtgctg | 540 |
| gattacttct | cagacactgt | ttatattgca | gacctcatca | ttcggctgcg | cacaggcttc | 600 |
| ctagaacaag | ggctcctggt | caaagacccc | aagaaattgc | gagacaacta | tatccacact | 660 |
| ttgcagttca | aattggatgt | ggcttctatc | atccccactg | acctcattta | ttttgctgtg | 720 |
| ggtatccaca | gccctgaggt | acgctttaat | cgtctgttac | actttgcccg | tatgtttgag | 780 |
| ttctttgacc | gcactgagac | acgtacaagc | taccccaaca | tcttccgaat | cagcaacctg | 840 |
| gtcctctaca | tcttggtcat | catccactgg | aatgcttgta | tttactatgc | tatctctaag | 900 |
| tccattggct | ttgggggtga | cacctgggtt | taccccaaca | ttactgaccc | tgaatatggc | 960 |
| tacctggcta | gggagtacat | ttactgcctt | tactggtcca | cactgaccct | caccaccatt | 1020 |
| ggagagacac | caccccctgt | aaaggatgag | gagtacctat | ttgtcatctt | tgacttcctg | 1080 |
| attggtgtcc | tcatctttgc | cactattgtg | ggaaatgtgg | gctccatgat | ctccaacatg | 1140 |
| aatgccacac | gagcagagtt | ccaggccaag | attgatgctg | tcaaacacta | catgcagttc | 1200 |
| cgaaaggtca | gtaaagacat | ggaagccaag | gtcatcaaat | ggtttgacta | cttgtggacc | 1260 |
| aataagaaga | cagtagatga | acgagaagtc | ctaaagaacc | tgcctgcaaa | gcttagggca | 1320 |
| gagatagcca | ttaatgttca | tttgtccact | ctgaagaaag | tgcgcatatt | ccaggattgt | 1380 |
| gaagctggcc | tgctggtgga | actggtactg | aagcttcgtc | ctcaggtctt | tagtcctgga | 1440 |
| gattatattt | gccgtaaggg | ggacattggc | aaggaaatgt | acatcatcaa | ggagggcaaa | 1500 |
| ttggcagtgg | tagctgatga | tggtgtgact | cagtatgcct | tgctgtcagc | tgggagctgc | 1560 |
| tttggtgaga | ttagtatcct | taacattaag | ggtagcaaaa | tgggcaatcg | gcgcactgcc | 1620 |
| aatatccgta | gtctgggcta | ctcagatctc | ttctgcttgt | ccaaggatga | tcttatggaa | 1680 |
| gctgtgactg | agtatcctga | tgccaagaaa | gtcctggaaa | acggggtag | ggagatcctg | 1740 |
| atgaaggaag | gtctactgga | tgagaatgaa | gtggcagcta | gtatggaggt | agatgttcag | 1800 |
| gagaagctgg | agcagctgga | gacaaacatg | gagaccttgt | acactcgttt | tgcccgcctg | 1860 |
| ctggctgagt | acactggagc | ccagcagaag | ctcaaacagc | gcatcacagt | gctggagacc | 1920 |
| aagatgaaac | agaaccatga | ggatgattac | ctatcagatg | ggataaacac | ccctgagcca | 1980 |
| gctgttgctg | aatag | | | | | 1995 |

<210> SEQ ID NO 5
<211> LENGTH: 1740
<212> TYPE: DNA
<213> ORGANISM: Human

<400> SEQUENCE: 5

| | | | | | |
|---|---|---|---|---|---|
| cttgctcctc | aggcagaggc | tgagtccgca | catcacctcc | aggccctcag | aacacctgcc | 60 |
| ccagccccac | catgctcatg | gcgtccacca | cttccgctgt | gcctgggcat | ccctctctgc | 120 |
| ccagcctgcc | cagcaacagc | agccaggaga | ggccactgga | cacccgggac | ccgctgctag | 180 |
| cccgggcgga | gctggcgctg | ctctccatag | tctttgtggc | tgtggccctg | agcaatggcc | 240 |
| tggtgctggc | ggccctagct | cggcggggcc | ggcggggcca | ctgggcaccc | atacacgtct | 300 |
| tcattggcca | cttgtgcctg | gccgacctgg | ccgtggctct | gttccaagtg | ctgccccagc | 360 |
| tggcctggaa | ggccaccgac | cgcttccgtg | gccagatgc | cctgtgtcgg | gccgtgaagt | 420 |
| atctgcagat | ggtgggcatg | tatgcctcct | cctacatgat | cctggccatg | acgctggacc | 480 |
| gccaccgtgc | catctgccgt | ccatgctgg | cgtaccgcca | tggaagtggg | gctcactgga | 540 |
| accggccggt | gctagtggct | tgggccttct | cgctccttct | cagcctgccc | cagctcttca | 600 |
| tcttcgccca | gcgcaacgtg | gaaggtggca | gcggggtcac | tgactgctgg | gcctgctttg | 660 |
| cggagccctg | gggccgtcgc | acctatgtca | cctggattgc | cctgatggtg | ttcgtggcac | 720 |
| ctaccctggg | tatcgccgcc | tgccaggtgc | tcatcttccg | ggagattcat | gccagtctgg | 780 |
| tgccagggcc | atcagagagg | cctgggggc | gccgcagggg | acgccggaca | ggcagccccg | 840 |
| gtgagggagc | ccacgtgtca | gcagctgtgg | ccaagactgt | gaggatgacg | ctagtgattg | 900 |
| tggtcgtcta | tgtgctgtgc | tgggcaccct | tcttcctggt | gcagctgtgg | gccgcgtggg | 960 |
| acccggaggc | acctctggaa | ggtgggtgta | gccgtggcta | gggctgacgg | ggccacttgg | 1020 |
| gcttggccgc | atgcccctgt | gccccaccag | ccatcctgaa | cccaacctag | atcctccacc | 1080 |
| tccacagggg | cgcccttttgt | gctactcatg | ttgctggcca | gcctcaacag | ctgcaccaac | 1140 |
| ccctggatct | atgcatcttt | cagcagcagc | gtgtcctcag | agctgcgaag | cttgctctgc | 1200 |
| tgtgcccggg | gacgcacccc | acccagcctg | gtccccaag | atgagtcctg | caccaccgcc | 1260 |
| agctcctccc | tggccaagga | cacttcatcg | tgaggagctg | ttgggtgtct | tgcctctaga | 1320 |
| ggctttgaga | agctcagctg | ccttcctggg | gctggtcctg | ggagccactg | gagggggac | 1380 |
| ccgtggagaa | ttggccagag | cctgtggccc | cgaggctggg | acactgtgtg | gccctggaca | 1440 |
| agccacagcc | cctgcctggg | tctccacatc | cccagctgta | tgaggagagc | ttcaggcccc | 1500 |
| aggactgtgg | gggcccctca | ggtcagctca | ctgagctggg | tgtaggaggg | gctgcagcag | 1560 |
| aggcctgagg | agtggcagga | aagagggagc | aggtgccccc | aggtgagaca | gcggtcccag | 1620 |
| gggcctgaaa | aggaaggacc | aggctgggc | caggggacct | tcctgtctcc | gcctttctaa | 1680 |
| tccctccctc | ctcattctct | ccctaataaa | aattggagct | cattttccac | aaaaaaaaaa | 1740 |

<210> SEQ ID NO 6
<211> LENGTH: 1995
<212> TYPE: DNA
<213> ORGANISM: Artificial
<220> FEATURE:
<223> OTHER INFORMATION: modified CNG alpha2

<400> SEQUENCE: 6

| | | | | | |
|---|---|---|---|---|---|
| atgatgaccg | aaaaatccaa | cggtgtgaag | agctctccag | ctaataacca | taaccatcat | 60 |
| cctcctcctt | ctatcaaggc | caatggcaaa | gatgaccaca | gggcaggtag | cagaccacag | 120 |

| | |
|---|---|
| tctgtggcag ctgatgatga cacttcctca gaactgcaaa ggttggcaga gatggatact | 180 |
| ccacgcaggg gaaggggtgg cttccgaagg attgtccgcc tggtggggat catcagagac | 240 |
| tgggccaaca aaaatttccg tgaggaggaa ccaagacctg actccttcct agagcgtttc | 300 |
| cgtgggcctg agctccagac tgtgacaacc catcagggg atggcaaagg cgacaaggac | 360 |
| ggcgagggaa agggcaccaa aaagaaattt gaactgtttg ttttggaccc agctggagac | 420 |
| tggtattacc gttggttgtt tgtcattgcc atgcctgttc tttacaactg gtgtctgttg | 480 |
| gtagccagag cctgcttcag tgatctacag agaaactatt ttgtggtatg ctggtgctg | 540 |
| gattacttct cagacactgt ttatattgca gacctcatca ttcggctgcg cacaggcttc | 600 |
| ctagaacaag ggctcctggt caaagacccc aagaaattgc gagacaacta tatccacact | 660 |
| ttgcagttca aattggatgt ggcttctatc atccccactg acctcattta ttttgctgtg | 720 |
| ggtatccaca gccctgaggt acgctttaat cgtctgttac actttgcccg tatgtttgag | 780 |
| ttctttgacc gcactgagac acgtacaagc taccccaaca tcttccgaat cagcaacctg | 840 |
| gtcctctaca tcttggtcat catccactgg aatgcttgta tttactatgc tatctctaag | 900 |
| tccattggct ttggggttga cacctgggtt taccccaaca ttactgaccc tgaatatggc | 960 |
| tacctggcta gggagtacat ttactgcctt tactggtcca cactgaccct caccaccatt | 1020 |
| ggagagacac cacccctgt aaaggatgag gagtacctat ttgtcatctt tgacttcctg | 1080 |
| attggtgtcc tcatctttgc cactattgtg gaaatgtgg gctccatgat ctccaacatg | 1140 |
| aatgccacac gagcagagtt ccaggccaag attgatgctg tcaaacacta catgcagttc | 1200 |
| cgaaaggtca gtaagacat ggaagccaag gtcatcaaat ggtttgacta cttgtggacc | 1260 |
| aataagaaga cagtagatga acgagaagtc ctaaagaacc tgcctgcaaa gcttagggca | 1320 |
| gagatagcca ttaatgttca tttgtccact ctgaagaaag tgcgcatatt ccaggattgg | 1380 |
| gaagctggcc tgctggtgga actggtactg aagcttcgtc ctcaggtctt tagtcctgga | 1440 |
| gattatattt gccgtaaggg ggacattggc aaggaaatgt acatcatcaa ggagggcaaa | 1500 |
| ttggcagtgg tagctgatga tggtgtgact cagtatgcct tgctgtcagc tgggagctgc | 1560 |
| tttggtgaga ttagtatcct taacattaag ggtagcaaaa tgggcaatcg gcgcactgcc | 1620 |
| aatatccgta gtctgggcta ctcagatctc ttctgcttgt ccaaggatga tcttatggaa | 1680 |
| gctgtgactg agtatcctga tgccaagaaa gtcctggaag aacggggtag ggagatcctg | 1740 |
| atgaagatgg gtctactgga tgagaatgaa gtggcagcta gtatggaggt agatgttcag | 1800 |
| gagaagctgg agcagctgga gacaaacatg gagaccttgt acactcgttt tgcccgcctg | 1860 |
| ctggctgagt acactggagc ccagcagaag ctcaaacagc gcatcacagt gctggagacc | 1920 |
| aagatgaaac agaaccatga ggatgattac ctatcagatg ggataaacac ccctgagcca | 1980 |
| gctgttgctg aatag | 1995 |

<210> SEQ ID NO 7
<211> LENGTH: 687
<212> TYPE: DNA
<213> ORGANISM: Artificial
<220> FEATURE:
<223> OTHER INFORMATION: modified aequorin

<400> SEQUENCE: 7

| | |
|---|---|
| atgagcgtgc tgacccccct gctgctgcgc ggcctgaccg gcagcgcccg ccgcctgccc | 60 |
| gtgcccgcg ccaagatcca cagcctgccc ccgagggca gctgggcat catgaaggtg | 120 |
| aagctgacca gcgacttcga caacccccaag tggatcggcc gccacaagca catgttcaac | 180 |

-continued

```
ttcctggacg tgaaccacaa cggccgcatc agcctggacg agatggtgta caaggccagc    240
gacatcgtga tcaacaacct gggcgccacc cccgagcagg ccaagcgcca aggacgcc     300 gtggaggcct tcttcggcgg cgccggcatg aagtacggcg tggagaccga gtggcccgag    360
tacatcgagg ctggaagcg cctggccacc gaggagctgg agcgctacag caagaaccag    420
atcaccctga tccgcctgtg gggcgacgcc ctgttcgaca tcatcgacaa ggaccagaac    480
ggcgccatca ccctggacga gtggaaggcc tacaccaaga gcgccggcat catccagagc    540
agcgaggact gcgaggagac cttccgcgtg tgcgacatcg acgagagcgg ccagctggac    600
gtggacgaga tgacccgcca gcacctgggc ttctggtaca ccatggaccc cgcctgcgag    660
aagctgtacg gcggcgccgt gccctaa                                        687
```

<210> SEQ ID NO 8
<211> LENGTH: 463
<212> TYPE: PRT
<213> ORGANISM: Human

<400> SEQUENCE: 8

```
Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Ala Thr Leu Phe Cys Asn Arg
50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
                85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Leu Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
```

-continued

```
            275                 280                 285
Tyr Leu Tyr Glu Asp Glu Gly Cys Trp Thr Arg Asn Ser Asn Met Asn
            290                 295                 300
Tyr Trp Leu Ile Ile Arg Leu Pro Ile Leu Phe Ala Ile Gly Val Asn
305                 310                 315                 320
Phe Leu Ile Phe Val Arg Val Ile Cys Ile Val Ser Lys Leu Lys
                325                 330                 335
Ala Asn Leu Met Cys Lys Thr Asp Ile Lys Cys Arg Leu Ala Lys Ser
            340                 345                 350
Thr Leu Thr Leu Ile Pro Leu Leu Gly Thr His Glu Val Ile Phe Ala
            355                 360                 365
Phe Val Met Asp Glu His Ala Arg Gly Thr Leu Arg Phe Ile Lys Leu
            370                 375                 380
Phe Thr Glu Leu Ser Phe Thr Ser Phe Gln Gly Leu Met Val Ala Ile
385                 390                 395                 400
Leu Tyr Cys Phe Val Asn Asn Glu Val Gln Leu Glu Phe Arg Lys Ser
                405                 410                 415
Trp Glu Arg Trp Arg Leu Glu His Leu His Ile Gln Arg Asp Ser Ser
            420                 425                 430
Met Lys Pro Leu Lys Cys Pro Thr Ser Ser Leu Ser Ser Gly Ala Thr
            435                 440                 445
Ala Gly Ser Ser Met Tyr Thr Ala Thr Cys Gln Ala Ser Cys Ser
            450                 455                 460

<210> SEQ ID NO 9
<211> LENGTH: 1392
<212> TYPE: DNA
<213> ORGANISM: Human

<400> SEQUENCE: 9
atggccggcg cccccggccc gctgcgcctt gcgctgctgc tgctcgggat ggtgggcagg     60
gccggccccc gccccagggt gccactgtg tccctctggg agacggtgca gaaatggcga    120
gaataccgac gccagtgcca gcgctccctg actgaggatc cacctcctgc cacagacttg    180
ttctgcaacc ggaccttcga tgaatacgcc tgctggccag atgggggagcc aggctcgttc    240 gtgaatgtca gctgccctg gtacctgccc tgggccagca gtgtgccgca gggccacgtg    300
taccggttct gcacagctga aggcctctgg ctgcagaagg acaactccag cctgccctgg    360
agggacttgt cggagtgcga ggagtccaag cgaggggaga aagctcccc ggaggagcag    420 ctcctgttcc tctacatcat ctacacggtg ggctacgcac tctccttctc tgctctggtt    480
atcgcctctg cgatcctcct cggcttcaga cacctgcact gcacccggaa ctacatccac    540
ctgaacctgt ttgcatcctt catcctgcga gcattgtccg tcttcatcaa ggacgcagcc    600
ctgaagtgga tgtatagcac agccgcccag cagcaccagt gggatgggct cctctcctac    660
caggactctc tgagctgccg cctggtgttt ctgctcatgc agtactgtgt ggcggccaat    720
tactactggc tcttggtgga gggcgtgtac ctgtacacac tgctggcctt tcggtcttc    780 tctgagcaat ggatcttcag gctctacgtg agcataggct ggggtgttcc cctgctgttt    840
gttgtcccct gggcattgt caagtacctc tatgaggacg agggctgctg gaccaggaac    900
tccaacatga actactggct cattatccgg ctgcccattc tctttgccat tggggtgaac    960
ttcctcatct ttgttcgggt catctgcatc gtggtatcca aactgaaggc caatctcatg   1020
tgcaagacag acatcaaatg cagacttgcc aagtccacgc tgacactcat ccccctgctg   1080
```

-continued

```
gggactcatg aggtcatctt tgcctttgtg atggacgagc acgcccgggg gaccctgcgc    1140
ttcatcaagc tgtttacaga gctctccttc acctccttcc aggggctgat ggtggccatc    1200
ttatactgct ttgtcaacaa tgaggtccag ctggaatttc ggaagagctg ggagcgctgg    1260
cggcttgagc acttgcacat ccagagggac agcagcatga agcccctcaa gtgtcccacc    1320
agcagcctga gcagtggagc cacggcgggc agcagcatgt acacagccac ttgccaggcc    1380
tcctgcagct ga                                                        1392
```

BIOASSAY METHOD FOR DETECTING PHYSIOLOGICALLY ACTIVE SUBSTANCE

TECHNICAL FIELD

The present invention relates to a cell expressing a receptor that alters intracellular cAMP concentration, a cAMP dependent calcium channel and a calcium sensitive protein, a composition comprising the cell, use of the composition for diagnosing a disease associated with a physiologically active substance that binds to the receptor, and a method for diagnosing the disease using the composition, etc.

BACKGROUND ART

Receptors to which physiologically active substances bind may serve as drug development targets. Particularly, receptors that alter intracellular cAMP concentration as second messengers, such as G protein-coupled receptors (hereinafter, also referred to as GPCRs), are important as drug development targets. Many agents that bind to such receptors have been developed so far. Examples of such GPCRs include receptors to which arginine vasopressin (hereinafter, also referred to as AVP) or glucagon-like peptide-1 (hereinafter, also referred to as GLP-1) binds.

Arginine vasopressin produced by the pituitary gland is a peptide hormone with a molecular weight of 1000 that is composed of 9 amino acids. AVP is one type of important water and electrolyte regulating hormone that performs water reabsorption in the kidney depending on decrease in circulating blood volume, a rise in plasma osmolality, etc. The assay of AVP in plasma is clinically applied widely to, for example, the diagnosis of disorders of water and electrolyte metabolism, such as diabetes insipidus which is a pathological condition involving the decreased secretion of AVP or the syndrome of inappropriate AVP secretion in which increase in AVP secretion is instead seen. Moreover, AVP is not only assayed for endocrine disease but also used as a marker for the prognosis of small-cell lung cancer or for acute heart failure. An ELISA kit by which chemically labeled AVP is allowed to compete with AVP in a sample and AVP is quantified on the basis of a competitive inhibition rate is widely used as a method for assaying AVP. However, the ELISA method using the competition technique has poor sensitivity and has limitations in the assay of a microscale sample in blood. Since AVP is a low-molecular-weight peptide, AVP in plasma cannot be assayed with high sensitivity due to the unavailability of sandwich ELISA assay using sandwich antibodies against a plurality of antigen determinants that permit higher sensitivity. Thus, a radioimmunoassay method using isotope-labeled AVP, which was developed by Robertson et al. in 1973, is still used widely in clinical practice as a method for assaying AVP in plasma (Non Patent Literature 1).

A V1a receptor, a V1b receptor and a V2 receptor (hereinafter, also referred to as V2R) are known as AVP receptors. A selective vasopressin V2 receptor antagonist tolvaptan has been reported to be effective for hyponatremia (heart failure, liver cirrhosis and the syndrome of inappropriate antidiuretic hormone secretion (SIADH)) (Non Patent Literature 2).

Incretin, one type of gastrointestinal hormone, is secreted from the intestinal tract in response to the stimulation of dietary intake and enhances insulin secretion from pancreatic beta cells. GLP-1 and GIP (gastric inhibitory peptide or glucose-dependent insulinotropic polypeptide) are known as major active molecules of incretin hormones. Among them, the GLP-1 peptide has received the highest attention as a blood glucose regulator.

GLP-1 not only promotes insulin secretion dependent on glucose but also participates in the inhibition of glucagon secretion from pancreatic alpha cells and further in the inhibition of gastric emptying. Moreover, GLP-1 can act centrally on the hypothalamus to suppress appetite, resulting in the control of weight gain. Since this series of physiological actions brings about desirable effect on the treatment of type 2 diabetes mellitus, drug development aimed at enhancing the action of GLP-1 has been carried out widely.

GLP-1 is secreted from intestinal L cells and converted to GLP-1 (7-37) or GLP-1 (7-36 amide) by processing. Both the forms have equivalent physiological activity against GLP-1 receptors. In blood, 80% or more of active forms of GLP-1 are the GLP-1 (7-36 amide) forms. These GLP-1 peptides are called "active forms of GLP-1". The active form of GLP-1 is immediately inactivated into GLP-1 (9-37 or 9-36 amide) through cleavage of its N-terminal moiety by dipeptidyl peptidase-IV (DPP-IV). In this regard, DPP-IV inhibitors aimed at enhancing the action of GLP-1 have been developed and clinically used widely (Non Patent Literature 3). Furthermore, GLP-1 derivatives resistant to DPP-IV have also been developed and come into action as clinical drugs. Moreover, agents targeting the action of enhancing GLP-1 secretion are also under clinical trial as next generation antidiabetic drugs (Non Patent Literature 4). Increase in demand in the near future for a method for accurately and rapidly measuring the serum concentration of the active form of GLP-1 is expected in the determination of the effect of these GLP-1 action enhancing drugs.

Moreover, the fasting serum concentration of the active form of GLP-1 has recently been reported to be much lower in Asians than in Westerners, suggesting that a highly sensitive assay method capable of detecting difference in the serum concentration of the active form of GLP-1 among races or among individuals will be required (Non Patent Literature 5).

An EIA (Enzyme Immuno Assay) kit based on a two-antibody sandwich method has already been launched as a method for measuring the serum concentration of the active form of GLP-1 before undergoing degradation. The existing kit is used in, for example, the determination of the effect of DPP-IV inhibitors that inhibit the degradation of GLP-1. The lowest detection sensitivity of the existing EIA method is approximately 1-2 pM (3.3-6.6 pg/ml) for the active form of GLP-1 (7-36 amide) and is also the same level for the GLP-1 (7-37) form. Since the fasting concentration of the active form of GLP-1 is 1 pM or lower in Asians, higher sensitivity is required for accurately measuring the fasting concentration of the active form of GLP-1. In this respect, the concentration and purification of a sample are necessary for the existing kit (Non Patent Literature 6).

CITATION LIST

Non Patent Literature

Non Patent Literature 1: Robertson, G. L., et al.: J. Clin. Invest., 52:2340, 1973

Non Patent Literature 2: Plosker G. L., Drugs. 70(4):443-54, 2010

Non Patent Literature 3: Chronic administration of alogliptin, a novel, potent, and highly selective dipeptidyl peptidase-4 inhibitor, improves glycemic control and beta-cell function in obese diabetic ob/ob mice. European Journal of Pharmacology 588, 325-332 (2008) Moritoh, Y. et al.

Non Patent Literature 4: Targeting GRP120 and other fatty acid-sensing GPCRs ameliorates insulin resistance and inflammatory diseases Trends in Pharmacol. Sci. 32,543-550 (2011) Talukdar, S. et al.

Non Patent Literature 5: Little enhancement of meal-induced glucagon-like pepide 1 secretion in Japanese: Comparison of type 2 diabetes patients and healthy controls. Journal of Diabetes investigation 1, 56-59 (2010) Yabe, D. et al.

Non Patent Literature 6: Analysis of glucagon-like peptide 1; what to measure? Clinica Chimica Acta 412, 1191-1194 (2011) Heijboer, A. C. et al.

SUMMARY OF INVENTION

Technical Problem to be Solved

An object of the present invention is to provide a composition for measurement of a physiologically active substance and a composition for clinical diagnosis, etc., which can be manipulated more conveniently than conventional methods without a use of a radioisotope that requires special techniques or equipment. Moreover, a further object of the present invention is to provide a method for diagnosing a disease associated with the physiologically active substance using the composition, etc.

Solution to Problem

The present inventors focused on the interaction among a receptor that alters intracellular cAMP concentration, a cAMP dependent calcium channel and a calcium sensitive protein and focused on V2R and a receptor to which GLP-1 binds (hereinafter, also referred to as a GLP-1 receptor) as examples of the receptor that alters intracellular cAMP concentration. The present inventors further used the calcium sensitive protein to measure the amount of calcium ion entry into a cell stimulated by cAMP which is formed by the binding of ligands to these receptors. As a result, the present inventors have successfully measured the amounts of the ligands, and consequently completed the present invention.

In one aspect, the present invention provides a cell expressing a receptor that alters intracellular cAMP concentration (hereinafter, also referred to as a "receptor which alters cAMP concentration"), a cAMP dependent calcium channel and a calcium sensitive protein, and a composition and a kit comprising the cell.

In one aspect, the present invention provides a composition and a kit for measuring the amount of a physiologically active substance that binds to the "receptor which alters cAMP concentration" in vitro, for measuring the activity of an agonist or an antagonist of the "receptor which alters cAMP concentration", for diagnosing a disease associated with the physiologically active substance or for determining therapeutic effect on and prognosis of a human under drug treatment of the disease, etc., comprising the cell expressing a "receptor which alters cAMP concentration", a cAMP dependent calcium channel and a calcium sensitive protein.

In one aspect, the present invention provides a method for measuring the amount of a physiologically active substance that binds to the "receptor which alters cAMP concentration" in a biological sample, a method for diagnosing a disease associated with the physiologically active substance, a method for determining a risk of developing a disease associated with the physiologically active substance or a method for determining the effectiveness of treatment of a disease associated with the physiologically active substance, etc., comprising the following steps (A) to (C):

(A) preparing a mixture containing a cell expressing a "receptor which alters cAMP concentration", a cAMP dependent calcium channel and a calcium sensitive protein, a luminescent substrate for the calcium sensitive protein, a $Ca^{2+}$-free medium and a biological sample derived from a test subject;
(B) adding a $Ca^{2+}$-containing solution to the mixture prepared in (A); and
(C) measuring the luminescence of the calcium sensitive protein emitted from the cell.

In one aspect, the present invention provides a method for screening for an agonist or an antagonist of the "receptor which alters cAMP concentration", comprising the following steps (A') to (C'):

(A') preparing a mixture containing a cell expressing a "receptor which alters cAMP concentration", a cAMP dependent calcium channel and a calcium sensitive protein, a luminescent substrate for the calcium sensitive protein, a $Ca^{2+}$-free medium and a test compound;
(B') adding a $Ca^{2+}$-containing solution to the mixture prepared in (A'); and
(C') measuring the luminescence of the calcium sensitive protein emitted from the cell.

In one aspect, the present invention provides a method for screening for an antagonist of the "receptor which alters cAMP concentration", etc., comprising the following steps (A") to (C"):

(A") preparing a mixture containing a cell expressing a "receptor which alters cAMP concentration", a cAMP dependent calcium channel and a calcium sensitive protein, a luminescent substrate for the calcium sensitive protein, a $Ca^{2+}$-containing medium, a physiologically active substance that binds to the "receptor which alters cAMP concentration" and a test compound;
(B") adding forskolin to the mixture prepared in (A"); and
(C") measuring the luminescence of the calcium sensitive protein emitted from the cell.

Effects of Invention

According to the present invention, the amount of a physiologically active substance that binds to a receptor that alters intracellular cAMP concentration can be measured by simple and safe procedures without the need of complicated procedures accompanied with use of radioisotopes.

DESCRIPTION OF EMBODIMENTS

Figure 1:
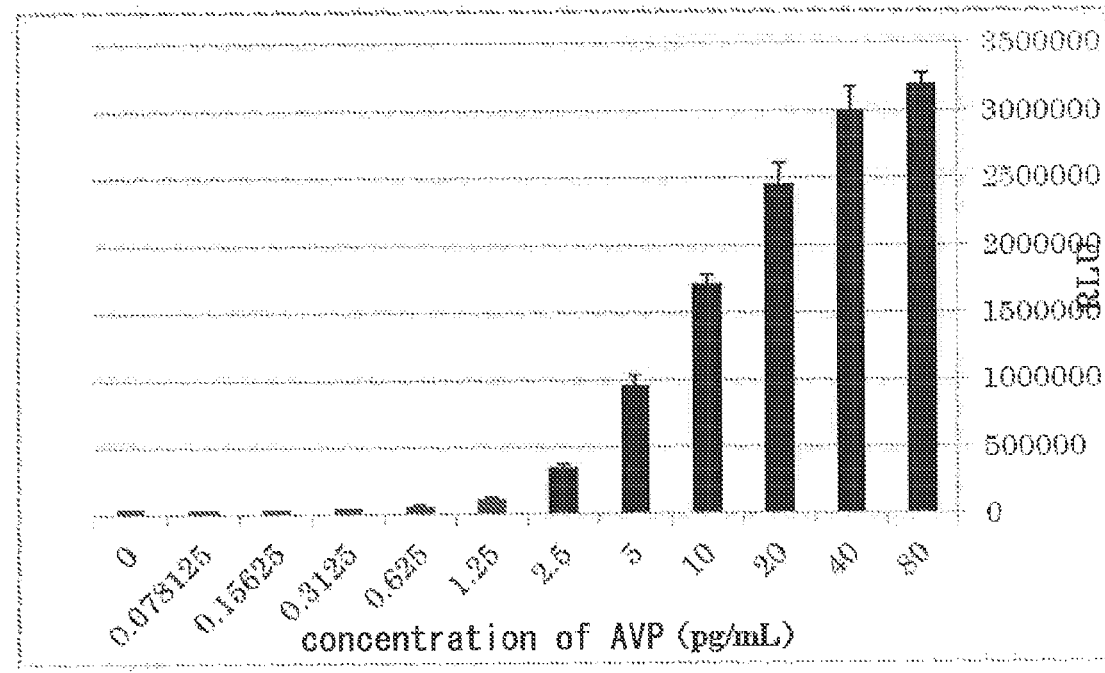
FIG. 1 shows that luminescence emitted from CHO cells expressing human V2R, modified CNG channel and modified aequorin is dependent on a concentration of AVP.

1. Cell Expressing "Receptor which Alters cAMP Concentration" to which Physiologically Active Substance Binds, cAMP Dependent Calcium Channel and Calcium Sensitive Protein, and Composition and Kit Comprising the Cell The present invention provides a cell expressing a "receptor which alters cAMP concentration" to which a physiologically active substance binds, a cAMP dependent calcium channel and a calcium sensitive protein, and a composition and a kit comprising the cell.

The physiologically active substance is a substance that exerts physiological action or pharmacological action on organisms. Examples of the physiologically active substance include physiologically active amines, amino acids acting as neurotransmitters, physiologically active peptides (e.g., vasopressin and incretin), lipid mediators and chemokines. Examples of the vasopressin include AVP. Examples of the incretin hormone include GLP-1-related peptides (e.g., GLP-1, GLP-1 degradation products, GLP-2, oxyntomodulin and glucagon) and GLP-1-like physiologically active peptide drugs (exenatide and liraglutide).

The "receptor which alters cAMP concentration" is a receptor that alters cAMP concentration in a cell expressing the receptor by the binding of a physiologically active substance as its ligand to the receptor. Examples of the "receptor which alters cAMP concentration" include receptors whose second messenger is cAMP, for example, GPCR whose second messenger is cAMP. Examples of the GPCR whose second messenger is cAMP include Gs-coupled GPCR.

Examples of the Gs-coupled GPCR include a vasopressin V2 receptor and a GLP-1 receptor.

In one embodiment, the present invention provides a cell expressing Gs-coupled GPCR, a cAMP dependent calcium channel and a calcium sensitive protein, and a composition and a kit comprising the cell.

Aside from the embodiment, theoretically, a ligand that binds to Gq-coupled GPCR may be quantified using a cell expressing Gq-coupled GPCR and a calcium sensitive protein. Specifically, calcium ion entry from the IP3 channel of the endoplasmic reticulum into the cytoplasm stimulated by the binding of the ligand to Gq-coupled GPCR can be detected using the calcium sensitive protein to quantify the ligand. However, the ligand can be quantified with higher sensitivity using the cell expressing Gs-coupled GPCR, a cAMP dependent calcium channel and a calcium sensitive protein, provided by the embodiment. For example, AVP can be detected with higher sensitivity by a system for detecting AVP using a cell expressing Gs-coupled GPCR V2R, a cAMP dependent calcium channel and a calcium sensitive protein than by a system for detecting AVP using a cell expressing Gq-coupled GPCR V1a (or V1b) and a calcium sensitive protein.

The physiologically active substance may be associated with a disease. As used herein, the disease associated with the physiologically active substance is not limited as long as it is a disease in which the physiologically active substance is involved. Examples of the disease associated with the physiologically active substance include a disease that is developed due to an abnormally large or small amount of the physiologically active substance, a disease whose pathological condition progresses due to an abnormally large or small amount of the physiologically active substance, a disease that is developed due to a lack of normal functions exerted by the physiologically active substance, and a disease whose pathological condition progresses due to a lack of normal functions exerted by the physiologically active substance. Examples of the disease associated with the physiologically active substance include the syndrome of inappropriate antidiuretic hormone (hereinafter, also referred to as ADH) secretion, diabetes insipidus and type 2 diabetes mellitus.

In one embodiment, the cell expressing a "receptor which alters cAMP concentration" to which a physiologically active substance binds, a cAMP dependent calcium channel and a calcium sensitive protein, and the composition and the kit comprising the cell, provided by the present invention, can be a cell, a composition and a kit for diagnosing a disease associated with the physiologically active substance.

2. Cell Expressing V2R, cAMP Dependent Calcium Channel and Calcium Sensitive Protein, and Composition and Kit Comprising the Cell In one embodiment, the present invention provides a cell expressing V2R, a cAMP dependent calcium channel and a calcium sensitive protein, and a composition and a kit comprising the cell.

V2R is one type of receptor to which AVP binds. This receptor increases cAMP by activating adenylate cyclase. The origin of V2R is not limited as long as it is a mammal. The origin can be, for example, a human, a mouse, bovine or a rat. Moreover, V2R may have one or several (e.g., 2, 3, 4, 5, 6, 7, 8, 9 or 10) amino acids modified (added, substituted, deleted, etc.) appropriately in the amino acid sequence, or V2R may be a protein that consists of an amino acid sequence having 70% or more, 80% or more, 85% or more, 90% or more, 95% or more, 98% or more, or 99% or more identity to the amino acid sequence of natural V2R; binds to AVP; and has the function of increasing cAMP through activation of adenylate cyclase.

V2R can be a protein having the amino acid sequence represented by SEQ ID NO: 1. Furthermore, V2R can be a protein that consists of an amino acid sequence having 70% or more, 80% or more, 85% or more, 90% or more, 95% or more, 98% or more, or 99% or more identity to the amino acid sequence represented by SEQ ID NO: 1; binds to AVP; and has the function of increasing cAMP through activation of adenylate cyclase.

As used herein, AVP is not particularly limited as long as it is derived from a mammal. AVP can be derived from, for example, a human, a mouse, bovine, or a rat. AVP may have one or several (e.g., 2, 3, 4, 5, 6, 7, 8, 9 or 10) amino acids modified (added, substituted, deleted, etc.) appropriately in the amino acid sequence, or may be a protein that consists of an amino acid sequence having 70% or more, 80% or more, 85% or more, 90% or more, 95% or more, 98% or more, or 99% or more identity to the amino acid sequence of natural AVP; binds to V2R; and has the function of increasing cAMP through activation of adenylate cyclase.

The cAMP dependent calcium channel is a channel that changes the amount of calcium ion entry into a cell in response to change in the concentration of cAMP, and includes channels that increase the amount of calcium ion entry into a cell in response to increase in the concentration of cAMP. Examples of the cAMP dependent calcium channel include a CNG (cyclic nucleotide gated ion channel) calcium channel. The CNG calcium channel may have one or several (e.g., 2, 3, 4, 5, 6, 7, 8, 9 or 10) amino acids modified (added, substituted, deleted, etc.) in the amino acid sequence and may be modified (including substituted, added, and deleted) such that it exhibits, for example, higher sensitivity to cAMP than cGMP. The CNG calcium channel can be a protein that consists of an amino acid sequence having 70% or more, 80% or more, 85% or more, 90% or more, 95% or more, 98% or more, or 99% or more identity to the amino acid sequence of the natural CNG calcium channel and increases the amount of calcium ion entry into a cell in response to increase in the concentration of cAMP. Examples of the modification include the substitution of the 460th cysteine in a mouse CNG calcium channel with tryptophan, the substitution of the 583rd glutamic acid in a mouse CNG calcium channel with methionine, the substitution of the 537th threonine in a bovine CNG calcium channel with serine, methionine, valine, or alanine, and combinations thereof. These substitutions exemplified above are not limited to the animal species in which the substitutions are found respectively, and are also applicable to amino acid substitution at corresponding sites in other animal species. For example, threonine in a mouse CNG calcium channel corresponding to the 537th threonine in the bovine CNG calcium channel can be substituted with serine, methionine, valine, or alanine. Such substitution can be performed at one or more position(s). For example, the substitution of the 460th cysteine in the mouse CNG calcium channel with tryptophan is performed, and the substitution of the 583rd glutamic acid with methionine can also be performed.

The CNG calcium channel can consist of an α-subunit and/or a β-subunit. It may be of any constitution, for example, consisting of at least one subunit selected from the group consisting of an α2 subunit, an α3 subunit, an α4 subunit, and a β1b subunit. Furthermore, the subunit may be modified as described above.

The origin of the CNG calcium channel is not particularly limited as long as it is a mammal. The origin can be, for example, a human, a mouse, bovine, a rat or a pig. The CNG calcium channel can be a protein having the amino acid sequence represented by SEQ ID NO: 2. Furthermore, the CNG calcium channel can be a protein that consists of an amino acid sequence having 70% or more, 80% or more, 85% or more, 90% or more, 95% or more, 98% or more, or 99% or more identity to the amino acid sequence represented by SEQ ID NO: 2 and increases the amount of calcium ion entry into a cell in response to increase in the concentration of cAMP.

The calcium sensitive protein includes proteins whose structure is changed in response to calcium, and includes proteins that emit luminescence in response to calcium and proteins that function as a so-called calcium sensor.

Examples of the calcium sensitive protein include aequorin, cameleon (Invitrogen Corp.), Case12 (Evrogen), a protein comprising two GFPs differing in color, bound to calcium sensitive calmodulin and a partial sequence of myosin light chain kinase binding thereto, a calcium sensitive protein comprising calmodulin bound to between the 144th and 146th residues in the amino acid sequence of GFP, and a protein of probe No. G3-85 or A1-2 described in Japanese Unexamined Patent Application Publication No. 2002-153279, and apoproteins thereof, if any, (e.g., apoaequorin).

The amino acid sequence of the calcium sensitive protein may be modified (added, substituted, deleted, etc.) appropriately according to the purpose or may be modified to increase the amount of luminescence and/or to improve an SN ratio. The modification includes the addition, substitution and deletion of one or several (e.g., 2, 3, 4, 5, 6, 7, 8, 9 or 10) amino acids in the amino acid sequence, and modification to a protein that consists of an amino acid sequence having 70% or more, 80% or more, 85% or more, 90% or more, 95% or more, 98% or more or 99% or more identity to the amino acid sequence of the natural calcium sensitive protein and emits luminescence in response to calcium. For example, the calcium sensitive protein may be modified such that its gene is optimized for human codon usage and it has a mitochondrial targeting signal.

The calcium sensitive protein can be a protein having the amino acid sequence represented by SEQ ID NO: 3. Furthermore, the calcium sensitive protein can be a protein that consists of an amino acid sequence having 70% or more, 80% or more, 85% or more, 90% or more, 95% or more, 98% or more, or 99% or more identity to the amino acid sequence represented by SEQ ID NO: 3 and emits luminescence in response to calcium.

The cell expressing V2R, a cAMP dependent calcium channel and a calcium sensitive protein provided by the present invention transiently or stably expresses each of V2R, the cAMP dependent calcium channel and the calcium sensitive protein.

The cell is not particularly limited and can be a cell line such as a CHO cell, a HEK293 cell, or a 3T3 cell.

For example, the cell expressing V2R, a cAMP dependent calcium channel and a calcium sensitive protein provided by the present invention can be a CHO cell stably expressing each protein, wherein V2R consists of the amino acid sequence represented by SEQ ID NO: 1, the cAMP dependent calcium channel is a modified CNG calcium channel consisting of the amino acid sequence represented by SEQ ID NO: 2 and the calcium sensitive protein is modified apoaequorin consisting of the amino acid sequence represented by SEQ ID NO: 3. Furthermore, the cell expressing V2R, a cAMP dependent calcium channel and a calcium sensitive protein provided by the present invention can be, for example, a CHO cell stably expressing V2R, the cAMP dependent calcium channel and the calcium sensitive protein, each of which is a protein that consists of an amino acid sequence having 70% or more, 80% or more, 85% or more, 90% or more, 95% or more, 98% or more, or 99% or more identity to the amino acid sequence of SEQ ID NOs: 1-3 and maintains the functions of V2R, the cAMP dependent calcium channel or the calcium sensitive protein.

Moreover, a cell naturally expressing one or more protein(s) selected from the group consisting of V2R, the cAMP dependent calcium channel and the calcium sensitive protein may be used. In this case, the cell expressing V2R, a cAMP dependent calcium channel and a calcium sensitive protein provided by the present invention can also be prepared by forcing the cell to transiently or stably express the protein(s) that are not expressed in the cell. Examples of such cell include a kidney-derived cell endogenously expressing V2R that is forced to transiently or stably express each of the cAMP dependent calcium channel and the calcium sensitive protein and an olfactory tissue-derived cell endogenously expressing the CNG calcium channel that is forced to transiently or stably express each of the V2R and the calcium sensitive protein.

The cell expressing V2R, a cAMP dependent calcium channel and a calcium sensitive protein provided by the present invention can be cryopreserved. The cryopreservation can be performed at −20° C. to −80° C., for example −80° C., in a cell cryopreservation solution. The cell cryopreservation solution is not limited and includes CELLBANKER (R) (Nippon Zenyaku Kogyo Co., Ltd.), BAMBANKER (R) (Lymphotec Inc.), Cellvation (R) (CELOX LABORATORIES, Inc.), CryoStor (R) (BIOLIFE SOLUTIONS Ltd.), etc. Cells can be cryopreserved in a large number of the same lot so that a cell-derived measurement error among compositions or kits is drastically reduced. As a result, the reproducibility of measurement results can be improved. Moreover, the cell expressing V2R, a cAMP dependent calcium channel and a calcium sensitive protein provided by the present invention maintains sensitivity sufficient for detecting AVP present in human blood, even after being cryopreserved and thawed using a warm bath or the like. Moreover, after thawing, the cell is merely transferred into an appropriate container and cultured for approximately 3 hours in an appropriate medium, and the state of the cell is not deteriorated by a reagent added for detecting AVP, or by human blood-derived components.

A composition comprising the cell expressing V2R, a cAMP dependent calcium channel and a calcium sensitive protein, provided by the present invention as described above, can be used for measuring the amount of AVP in vitro, for determining either a hypotonic or hypertonic fluid infusion to be selected, for measuring the activity of a V2R agonist or antagonist, for diagnosing an AVP-associated disease, for determining a human having a high risk of developing an AVP-associated disease and/or for determining therapeutic effect on a human under treatment.

Accordingly, in an alternative embodiment, the present invention provides a composition and a kit for measuring the amount of AVP in vitro, for determining either a hypotonic or hypertonic fluid infusion to be selected, for measuring the activity of a V2R agonist or antagonist, for diagnosing an AVP-associated disease, for determining a human having a high risk of developing an AVP-associated disease or for determining therapeutic effect on a human under treatment of an AVP-associated disease, comprising the cell expressing V2R, a cAMP dependent calcium channel and a calcium sensitive protein.

The cell expressing V2R, a cAMP dependent calcium channel and a calcium sensitive protein is as described above.

The AVP-associated disease includes a disease involving the abnormal production or action of AVP. Examples of the AVP-associated disease include the syndrome of inappropriate antidiuretic hormone (hereinafter, also referred to as ADH) secretion (hereinafter, also referred to as SIADH) and diabetes insipidus.

SIADH is a disease that is developed due to the inappropriately increasing secretion of AVP or abnormally increased renal sensitivity to AVP. Typically, SIADH does not occur as a single disease and is developed as a complication or partial symptom of a different disease. For example, SIADH is developed in association with diseases such as lung diseases (e.g., pneumonia and pulmonary tuberculosis), central nervous diseases (e.g., meningitis) and ectopic antidiuretic hormone producing tumors (e.g., lung cancer (e.g., small-cell lung cancer) and pancreatic cancer) or in association with drug treatment (e.g., treatment with vincristine and clofibrate). SIADH is diagnosed on the basis of, for example, the following diagnostic criteria (Table 1).

TABLE 1

Criteria for diagnosis of SIADH

Excerpts from Companion of diagnosis of syndrome of inappropriate vasopression secretion (SIADH)[Note]
I. Main symptom 1. Symptoms of hyponatremia such as fatigue, loss of appetite and disturbed consciousness, which are not specific
2. Dehydration not found
II. Examination findings 1. Hyponatremia: Serum sodium concentration falls below 135 mEq/L.
2. Plasma vasopressin level: Serum sodium level is less than 135 mEq/L and plasma vasopressin level is equal to or higher than measurement sensitivity.
**3. Low plasma osmolality: Plasma osmolality falls below 280 mOsm/kg.
4. Hypersthenuria: Urine osmolality exceeds 300 mOsm/kg.
5. Sustention of natriuresis: Sodium concentration in urine is 20 mEq/L or higher.
6. Normal renal function: Serum creatinine level is 1.2 mg/dL or lower.
7. Normal adrenal cortical function: Serum cortisol level is 6 µg/dL or higher.
[Diagnostic criteria]

Definite diagnosis is made when the findings 1 to 7 of II are present and dehydration is not found.
[Differential diagnosis] The followings leading to hyponatremia are excluded:

1. Hyponatremia with an excess of an extracellular fluid: Heart failure, liver cirrhosis during ascites retention, and nephrotic syndrome
2. Hyponatremia with marked sodium leak: Renal sodium loss, diarrhea and vomiting

[**Note]
*Health and Labour Sciences Research Grants for Research on Measures for Intractable Diseases from the Ministry of Health Labour and Welfare of Japan Survey and Research on Diencephalic Pituitary Dysfunction: 2008 Annual Report of Research*: March 2009: p. 124

The diabetes insipidus is a disease involving excessive urination resulting from the reduced synthesis or action of AVP. The diabetes insipidus includes central diabetes insipidus and renal diabetes insipidus. The central diabetes insipidus is diagnosed by, for example, 1. confirmation of excessive urination (3 L/day or larger), 2. urinary test: negative for glucose in urine and low urine osmolality, 3. confirmation of AVP secretory dysfunction by a loading test with 5% hypertonic saline, 4. search for a lesion in a region of the hypothalamus or the pituitary gland by diagnostic imaging (MRI), and 5. confirmation of the ability to concentrate urine by the administration of desmopressin.

The amount of AVP can be measured in vitro by use of the following event:

When AVP is present in a biological sample, AVP increases cAMP by acting on V2R expressed in the cell provided by the present invention. As a result, the CNG calcium channel is activated so that calcium entry into the cell is increased. Thus, the calcium sensitive protein emits luminescence. This means that the presence of AVP in the sample is represented by the luminescence of the calcium sensitive protein as an output.

In one embodiment of the present invention, use of the composition provided by the present invention based on the phenomenon described above can measure the amount of AVP in a biological sample.

As used herein, the biological sample includes organism-derived samples such as blood, urine and a sample prepared from blood or blood and includes, for example, human blood, a sample prepared from human blood, human urine, and a sample prepared from human urine. The biological sample may be diluted appropriately with an appropriate aqueous solution. For example, a human urine sample may be diluted 4 to 20-fold with physiological saline and used for the composition provided by the present invention.

Using the composition provided by the present invention, the amount of AVP in human blood or urine can be measured by use of the event to diagnose a test subject as having an AVP-associated disease (e.g., diabetes insipidus or SIADH) or not.

For example, when a test subject is suspected of having SIADH, the test subject can be diagnosed as having SIADH or not by use of the event described in (1) using the composition provided by the present invention by measuring the amount of luminescence of the calcium sensitive protein emitted from the cell treated with a blood sample of the test subject and the amount of luminescence of the calcium sensitive protein emitted from the cell treated with the same amount of a blood sample of a normal individual (standard) as that of the blood sample of the test subject. For example, when the amount of luminescence emitted from the cell treated with the blood sample of the test subject is higher than that emitted from the cell treated with the blood sample of the normal individual (standard), the serum concentration of AVP of the test subject can be determined to be higher than that of the normal individual. This constitutes grounds for the diagnosis of the test subject as SIADH.

Moreover, for example, when a test subject is suspected of having diabetes insipidus, the test subject can be diagnosed as having diabetes insipidus or not by use of the event described in (1) using the composition provided by the present invention by measuring the amount of luminescence of the calcium sensitive protein emitted from the cell treated with a blood sample of the test subject and the amount of luminescence of the calcium sensitive protein emitted from the cell treated with the same amount of a blood sample of a normal individual (standard) as that of the blood sample of the test subject. For example, when the amount of luminescence emitted from the cell treated with the blood sample of the test subject is lower than that emitted from the cell treated with the blood sample of the normal individual (standard), the serum concentration of AVP of the test subject can be determined to be lower than that of the normal individual. This constitutes grounds for the diagnosis of the test subject as diabetes insipidus.

For the measurement of the amount of luminescence, it is preferred to measure the integrated value for the given time. For example, the integrated value can be measured for 5 seconds, 10 seconds, 15 seconds, 20 seconds, 30 seconds, 40 seconds, 50 seconds, or 1 minute.

When a fluid infusion is administered to a patient diagnosed as SIADH using the composition provided by the present invention, a hypertonic fluid infusion is selected. When a fluid infusion is administered to a patient diagnosed as diabetes insipidus using the composition provided by the present invention, a hypotonic fluid infusion is selected. Accordingly, the composition provided by the present invention is used for determining either a hypotonic fluid infusion or a hypertonic fluid infusion to be administered to a patient.

Moreover, the amount of AVP in human blood or urine can be measured using the composition provided by the present invention to determine a human having a high risk of developing an AVP-associated disease, for example, a human having a high risk of developing SIADH or diabetes insipidus.

For example, when the serum concentration of AVP measured using the composition provided by the present invention in medical examination is lower than the numeric value of a patient with SIADH and higher than the numeric value of a normal individual, this person can be determined as a human having a high risk of developing SIADH. When the serum concentration of AVP is higher than the numeric value of a patient with diabetes insipidus and lower than the numeric value of a normal individual, this person can be determined as a human having a high risk of developing diabetes insipidus. Moreover, when the serum concentration of AVP is gradually increased over time, this person can be determined as a human having a high risk of developing SIADH. When the serum concentration of AVP is gradually decreased over time, this person can be determined as a human having a high risk of developing diabetes insipidus.

Furthermore, the amount of AVP in human blood or urine can be measured using the composition provided by the present invention to determine the effectiveness of treatment for a human under treatment of an AVP-associated disease, for example, a human with SIADH or diabetes insipidus under treatment thereof.

For example, the concentration of AVP in blood samples collected from the same individual both before and after treatment, and time-dependent change in the concentration can be measured using the composition provided by the present invention to determine the presence or absence of effectiveness of the treatment. For example, when the serum concentration of AVP measured using the composition provided by the present invention is lower after treatment than before treatment, the treatment of SIADH can be determined as being effective. When the serum concentration of AVP is higher after treatment than before treatment, the treatment of diabetes insipidus can be determined as being effective.

The activity of a V2R agonist or antagonist can be measured using the composition provided by the present invention. For example, the activity of a V2R agonist can be measured by adding the V2R agonist to the composition provided by the present invention in the absence of AVP and quantifying the luminescence of the calcium sensitive protein. Moreover, for example, the activity of a V2R antagonist can be measured by adding the V2R antagonist to the composition provided by the present invention in the presence of AVP and quantifying the luminescence of the calcium sensitive protein.

In an alternative embodiment, the present invention provides a kit that comprises a composition comprising the cell expressing V2R, a cAMP dependent calcium channel and a calcium sensitive protein provided by the present invention and can further comprise at least one selected from the group consisting of a medium for cell culture, a detection solution, a luminescent substrate for the calcium sensitive protein or an aqueous solution thereof, a plate for cell culture or a test tube, AVP or an aqueous solution thereof and a normal human control serum.

The kit can be prepared appropriately by those skilled in the art. For example, without limitations, each substance constituting the kit and the composition are individually packaged, and these packages can be placed together in one container such as a box to prepare a kit.

The composition comprising the cell expressing V2R, a cAMP dependent calcium channel and a calcium sensitive protein, provided by the present invention, can be prepared appropriately, and is prepared, without limitations, for example by suspending the cell at a density of $3 \times 10^6$ cells/ml in an aqueous solution. The medium for cell culture is not limited as long as it can maintain the cell provided by the present invention. The medium for cell culture can be $Ca^{2+}$-free or $Ca^{2+}/Mg^{2+}$-free.

The detection solution can contain $CaCl_2$, trypan blue, a cation that is capable of causing aequorin luminescence and can be substituted for calcium (e.g., a cadmium ion or a strontium ion), a magnesium ion, a zinc ion, a sulfate ion and/or a carbonate ion. The concentrations of $CaCl_2$ and trypan blue can be adjusted appropriately by those skilled in the art. For example, the concentration of $CaCl_2$ is 9 to 100 mM, and the concentration of trypan blue is 0.001 to 0.010%. The detection solution is, for example, an aqueous solution containing 9 mM $CaCl_2$ and 0.002% trypan blue. The final concentration of $CaCl_2$ when the amount of luminescence of the calcium sensitive protein is measured can be set to 3 to 33 mM. Further, the detection solution can contain a cation that can be substituted for calcium, a magnesium ion, a zinc ion, a sulfate ion and/or a carbonate ion, for example, by dissolving the cation that can be substituted for calcium, the magnesium ion, the zinc ion, the sulfate ion and/or the carbonate ion in the detection solution.

The luminescent substrate for the calcium sensitive protein includes coelenterazine or a coelenterazine derivative that serves as a luminescent substrate for aequorin. The coelenterazine derivative includes ViviRen (R), (Promega Corp.: 8-Benzyl-2-(4-hydroxybenzyl)-6-(4-hydroxyphenyl) imidazo[1,2-a]pyrazin-3-butyryloxymethyl ester). The concentration of the luminescent substrate (e.g., ViviRen) for the calcium sensitive protein can be set appropriately. The aqueous solution of the luminescent substrate for the calcium sensitive protein is, for example, an aqueous solution of 4 mM ViviRen (Promega Corp.).

Examples of the plate for cell culture include those allowing measurement of the amount of luminescence using a luminometer, for example, a 96-well plate allowing cell culture.

The test tube is not particularly limited and can be selected appropriately by those skilled in the art. For example, a test tube suitable for an apparatus for measuring luminescence emitted from the calcium sensitive protein can be used.

AVP is not limited as long as it can be used as a V2R agonist. AVP may be used as a positive control. AVP can be, but not limited to, human AVP. The concentration of AVP can be prepared appropriately by those skilled in the art.

The normal human control serum may be used as a negative control and can be prepared appropriately by those skilled in the art.

The kit provided by the present invention can be used in the same application as that of the composition provided by the present invention.

The composition or the kit provided by the present invention is also useful for diagnostic aid that helps a physician to differentiate an AVP-associated disease (e.g., SIADH or diabetes insipidus) from other diseases in view of clinical symptoms of the patient and/or other examination results. For example, the measurement of the amount of AVP in a blood sample of a patient exhibiting SIADH symptoms using the composition or the kit provided by the present invention can be useful for the differential diagnosis between SIADH and heart failure or the like. Moreover, the measurement of the amount of AVP in a blood sample of a patient exhibiting diabetes insipidus symptoms using the composition or the kit provided by the present invention can be useful for the differential diagnosis between diabetes insipidus and primary polydipsia or the like.

In one embodiment, the composition comprising the cell expressing V2R, a cAMP dependent calcium channel and a calcium sensitive protein, provided by the present invention, is capable of detecting AVP, a V2R agonist or a V2R antagonist with high sensitivity.

Accordingly, in a preferable embodiment, the kit provided by the present invention does not include an instrument or an apparatus for concentrating AVP, a V2R agonist or a V2R antagonist from a biological sample (e.g., columns (e.g., C18 columns such as Sep-Pak C18 columns) or an ultrafiltration apparatus).

3. Cell Expressing GLP-1 Receptor, cAMP Dependent Calcium Channel and Calcium Sensitive Protein, and Composition and Kit Comprising the Cell In one embodiment, the present invention provides a cell expressing a GLP-1 receptor, a cAMP dependent calcium channel and a calcium sensitive protein, and a composition and a kit comprising the cell.

The GLP-1 receptor is one type of receptor to which a GLP-1 peptide binds. This receptor increases cAMP by activating adenylate cyclase. The origin of the GLP-1 receptor is not limited as long as it is a mammal. The origin can be, for example, a human, a mouse, bovine or a rat. Moreover, the GLP-1 receptor may have one or several (e.g., 2, 3, 4, 5, 6, 7, 8, 9 or 10) amino acids modified (added, substituted, deleted, etc.) appropriately in the amino acid sequence, or the GLP-1 receptor may be a protein that consists of an amino acid sequence having 70% or more, 80% or more, 85% or more, 90% or more, 95% or more, 98% or more, or 99% or more identity to the amino acid sequence of the natural GLP-1 receptor; binds to GLP-1; and has the function of increasing cAMP through activation of adenylate cyclase.

The GLP-1 receptor can be a protein having the amino acid sequence represented by SEQ ID NO: 8. Furthermore, the GLP-1 receptor can be a protein that consists of an amino acid sequence having 70% or more, 80% or more, 85% or more, 90% or more, 95% or more, 98% or more, or 99% or more identity to the amino acid sequence represented by SEQ ID NO: 8; binds to GLP-1; and has the function of increasing cAMP through activation of adenylate cyclase.

As used herein, the GLP-1-related peptide is not limited as long as it is derived from a mammal. The GLP-1-related peptide can be derived from, for example, a human, a mouse, bovine, a rat or a rabbit. GLP-1 may have one or several (e.g., 2, 3, 4, 5, 6, 7, 8, 9 or 10) amino acids modified (added, substituted, deleted, etc.) appropriately in the amino acid sequence or may have a modifying group such as fatty acid introduced in an amino acid in the peptide. Alternatively, GLP-1 may be a protein that consists of an amino acid sequence having 70% or more, 80% or more, 85% or more, 90% or more, 95% or more, 98% or more, or 99% or more identity to the amino acid sequence of natural GLP-1; binds to a GLP-1 receptor; and has the function of increasing cAMP through activation of adenylate cyclase. Moreover, the GLP-1-like physiologically active peptide drug is not limited to a mammal-derived one and may be derived from, for example, a lizard or may be a protein having 50, 60, 70, 80, 90, 95 or 98% or more amino acid sequence identity to natural GLP-1; binds to a GLP-1 receptor; and has the function of increasing cAMP through activation of adenylate cyclase. Examples of the GLP-1-like physiologically active peptide drug include exenatide and liraglutide.

Those described above in "2. Cell expressing V2R, cAMP dependent calcium channel and calcium sensitive protein, and composition and kit comprising the cell" can be used as the cAMP dependent calcium channel and the calcium sensitive protein.

The cell expressing a GLP-1 receptor, a cAMP dependent calcium channel and a calcium sensitive protein, provided by the present invention, transiently or stably expresses each of the GLP-1 receptor, the cAMP dependent calcium channel and the calcium sensitive protein. The cell is not limited and can be a cell line such as a CHO cell, a HEK293 cell, or a 3T3 cell. For example, the cell expressing a GLP-1 receptor, a cAMP dependent calcium channel and a calcium sensitive protein, provided by the present invention, can be a CHO cell stably expressing each protein, wherein the GLP-1 receptor consists of the amino acid sequence represented by SEQ ID NO: 8, the cAMP dependent calcium channel is a modified CNG calcium channel consisting of the amino acid sequence represented by SEQ ID NO: 2, and the calcium sensitive protein is modified apoaequorin consisting of the amino acid sequence represented by SEQ ID NO: 3. Furthermore, the GLP-1 receptor cell provided by the present invention can be, for example, a CHO cell stably expressing the GLP-1 receptor, the cAMP dependent calcium channel and the calcium sensitive protein, each of which is a protein that consists of an amino acid sequence having 70% or more, 80% or more, 85% or more, 90% or more, 95% or more, 98% or more, or 99% or more identity to the amino acid sequence of any one of SEQ ID NOs: 8, 2 and 3 and maintains the functions of the GLP-1 receptor, the cAMP dependent calcium channel or the calcium sensitive protein.

Moreover, a cell naturally expressing one or more protein(s) selected from the group consisting of the GLP-1 receptor, the cAMP dependent calcium channel and the calcium sensitive protein may be used. In this case, the cell expressing a GLP-1 receptor, a cAMP dependent calcium channel and a calcium sensitive protein, provided by the present invention, can also be prepared by forcing the cell to transiently or stably express the protein(s) that are not expressed in the cell. Examples of such a cell include a pancreas-derived cell endogenously expressing the GLP-1 receptor that is forced to transiently or stably express each of the cAMP dependent calcium channel and the calcium sensitive protein and an olfactory tissue-derived cell endogenously expressing the CNG calcium channel that is forced to transiently or stably express each of the GLP-1 receptor and the calcium sensitive protein.

The cell expressing a GLP-1 receptor, a cAMP dependent calcium channel and a calcium sensitive protein, provided by the present invention, can be cryopreserved. The cryopreservation can be carried out similarly to the cell expressing V2R, a cAMP dependent calcium channel and a calcium sensitive protein as described above in "2. Cell expressing V2R, cAMP dependent calcium channel and calcium sensitive protein, and composition and kit comprising the cell".

The cell expressing a GLP-1 receptor, a cAMP dependent calcium channel and a calcium sensitive protein, provided by the present invention, maintains sensitivity sufficient for detecting GLP-1 present in human blood, even after being cryopreserved and thawed using a warm bath or the like. Moreover, after thawing, the cell is merely transferred into an appropriate container and cultured for several hours in an appropriate medium, and the state of the cell is not deteriorated by a reagent added for detecting GLP-1, or by human blood-derived components.

The present invention provides a composition and a kit for measuring the amount of an active form of GLP-1 in vitro, for measuring the activity of a GLP-1 receptor agonist or antagonist or for determining therapeutic effect on a human under treatment of a GLP-1-associated disease, comprising the cell expressing a GLP-1 receptor, a cAMP dependent calcium channel and a calcium sensitive protein.

The cell expressing a GLP-1 receptor, a cAMP dependent calcium channel and a calcium sensitive protein is as described above.

The GLP-1-associated disease includes a disease that is desirably treated by enhancement in the action of GLP-1, such as type 2 diabetes mellitus.

In the treatment of type 2 diabetes mellitus, an inhibitor of DPP-IV, which is a GLP-1 degrading enzyme, is used for the purpose of enhancing the action of GLP-1. Alternatively, a GLP-1 analog having resistance to degradation by DPP-IV is used in the treatment thereof.

The amount of GLP-1 can be measured in vitro by use of the following event:

When the active form of GLP-1 is present in a biological sample, the active form of GLP-1 increases cAMP by acting on the GLP-1 receptor expressed in the cell provided by the present invention. As a result, the CNG calcium channel is activated so that calcium entry into the cell is increased. Thus, the calcium sensitive protein emits luminescence. This means that the presence of the active form of GLP-1 in the sample is represented by the luminescence of the calcium sensitive protein as an output.

In one embodiment of the present invention, the amount of the active form of GLP-1 in a biological sample can be measured by use of the event using the composition provided by the present invention.

The biological sample is as described above in "2. Cell expressing V2R, cAMP dependent calcium channel and calcium sensitive protein, and composition and kit comprising the cell".

Furthermore, the active form of GLP-1 in human blood or urine can be assayed using the composition provided by the present invention to determine the effectiveness of treatment for a human under treatment of a GLP-1-associated disease, for example, a human with type 2 diabetes mellitus under treatment that increases the amount of an active form of GLP-1.

For example, the concentration of the active form of GLP-1 in blood samples collected from the same individual both before and after treatment, and time-dependent change in the concentration can be measured using the composition provided by the present invention to determine the presence or absence of effectiveness of the treatment. For example, when the serum concentration of the active form of GLP-1 measured using the composition provided by the present invention is higher after treatment than before treatment, a therapeutic drug that increases the amount of an active form of GLP-1 (e.g., a DPP-IV inhibitor) can be determined as being effective.

The activity of a GLP-1 agonist or antagonist can be measured using the composition provided by the present invention. For example, the activity of a GLP-1 agonist can be measured by adding the GLP-1 agonist to the composition provided by the present invention in the absence of GLP-1 and quantifying the amount of luminescence of the calcium sensitive protein. Moreover, for example, the activity of a GLP-1 antagonist can be measured by adding the GLP-1 antagonist to the composition provided by the present invention in the presence of GLP-1 and quantifying the amount of luminescence of the calcium sensitive protein.

The present invention provides a kit that comprises a composition comprising the cell expressing a GLP-1 receptor, a cAMP dependent calcium channel and a calcium sensitive protein and can further comprise at least one selected from a medium for cell culture, a detection solution, a luminescent substrate for the calcium sensitive protein or an aqueous solution thereof, a plate for cell culture or a test tube, GLP-1 or an aqueous solution thereof and a normal human control plasma.

The kit can be prepared appropriately by those skilled in the art. For example, without limitations, each substance constituting the kit and the composition are individually packaged, and these packages can be placed together in one container such as a box to prepare a kit.

GLP-1 is not limited as long as it can be used as a GLP-1 receptor agonist. GLP-1 may be used as a positive control. GLP-1 can be, but not limited to, human-derived GLP-1. The concentration of GLP-1 can be adjusted appropriately by those skilled in the art.

The other substances contained in the kit can be prepared with reference to the description of "2. Cell expressing V2R, cAMP dependent calcium channel and calcium sensitive protein, and composition and kit comprising the cell".

The kit provided by the present invention can be used in the same application as that of the composition provided by the present invention.

In one embodiment, the composition comprising the cell expressing a GLP-1 receptor, a cAMP dependent calcium channel and a calcium sensitive protein, provided by the present invention, is capable of detecting GLP-1, a GLP-1 receptor agonist or a GLP-1 receptor antagonist with high sensitivity.

Accordingly, in a preferable embodiment, the kit provided by the present invention does not include an instrument or an apparatus for concentrating GLP-1, a GLP-1 receptor agonist or a GLP-1 receptor antagonist from a biological sample (e.g., columns (e.g., C18 columns such as Sep-Pak C18 columns) or an ultrafiltration apparatus).

Furthermore, in one embodiment, the kit provided by the present invention is capable of measuring the total amount of both the active form of GLP-1 (7-36) and the active form of GLP-1 (7-37) by a single operation.

4. Bioassay Method Using Cell Expressing V2R, cAMP Dependent Calcium Channel and Calcium Sensitive Protein In one embodiment, the present invention also provides a method for measuring the amount of AVP in a biological sample, a method for diagnosing an AVP-associated disease, a method for determining a risk of developing an AVP-associated disease or a method for determining the effectiveness of treatment of an AVP-associated disease, comprising the following steps (A) to (C):

(A) preparing a mixture containing a cell expressing V2R, a cAMP dependent calcium channel and a calcium sensitive protein, a luminescent substrate for the calcium sensitive protein, a $Ca^{2+}$-free medium and a biological sample derived from a test subject;

(B) adding a $Ca^{2+}$-containing solution to the mixture prepared in (A); and (C) measuring the luminescence of the calcium sensitive protein emitted from the cell.

The materials used in the steps such as reagents, apparatuses or biological samples and conditions for the steps can be prepared or set appropriately by those skilled in the art with reference to the description of "2. Cell expressing V2R, cAMP dependent calcium channel and calcium sensitive protein, and composition and kit comprising the cell".

Examples of the $Ca^{2+}$-containing solution include a $CaCl_2$ solution.

The order of addition of the substances described in the step (A) of the method can be set appropriately by those skilled in the art.

The present invention provides, for example, a method for measuring the amount of AVP in a biological sample, a method for diagnosing an AVP-associated disease, a method for determining a risk of developing an AVP-associated disease or a method for determining the effectiveness of treatment of an AVP-associated disease, comprising the following steps:

(1) seeding, into a plate for cell culture, a cell expressing V2R, a cAMP dependent calcium channel and a calcium sensitive protein, the cell being suspended in a $Ca^{2+}$-free medium supplemented with a luminescent substrate for the calcium sensitive protein;

(2) adding a biological sample derived from a test subject to the cell and culturing the cell; and (3) adding a $CaCl_2$ solution to the cultured cell and measuring the luminescence of the calcium sensitive protein emitted from the cell.

The culture of the cell provided by the present invention may be sterile culture, but does not have to be sterile. For example, when the incubation time of the cell provided by the present invention is within 4 hours, sterile culture is not required for such a short time.

The luminescence is emitted by the calcium sensitive protein such as aequorin immediately after addition of the $CaCl_2$ solution and can be measured by a method which is well known by those skilled in the art. For example, a luminometer capable of automatically and continuously performing stirring and measurement (PerkinElmer Inc., ARVO-Sx) is used, and the amount of luminescence can be measured by integrating luminescence values for 15-30 seconds after stirring. The apparatus that can be used in the measurement of the amount of luminescence can be selected appropriately by those skilled in the art.

The amount of AVP in the biological sample is measured on the basis of the amount of luminescence of the calcium sensitive protein obtained as a result of carrying out the method. On the basis of the measured amount of AVP, an AVP-associated disease is diagnosed, a risk of developing an AVP-associated disease is determined or the effectiveness of treatment of an AVP-associated disease is determined. For example, when the amount of luminescence emitted from the cell treated with a blood sample of a test subject suspected of having SIADH is higher than that emitted from the cell treated with a blood sample of a normal individual (standard), the serum concentration of AVP of the test subject can be determined to be higher than that of the normal individual. Thus, the test subject is diagnosed as SIADH. Moreover, when the amount of luminescence emitted from the cell treated with a blood sample of a test subject suspected of having diabetes insipidus is lower than that emitted from the cell treated with a blood sample of a normal individual (standard), the serum concentration of AVP of the test subject can be determined to be lower than that of the normal individual. Thus, the test subject is diagnosed as diabetes insipidus.

In one embodiment, the composition comprising the cell expressing V2R, a cAMP dependent calcium channel and a calcium sensitive protein, provided by the present invention, is capable of detecting AVP, a V2R agonist or a V2R antagonist with high sensitivity.

Accordingly, in a preferable embodiment, the method provided by the present invention does not include the step of concentrating AVP, a V2R agonist or a V2R antagonist from a biological sample (e.g., the step of using columns (e.g., C18 columns such as Sep-Pak C18 columns), the step of using an ultrafiltration apparatus or the step of using a centrifugation concentration apparatus).

In an alternative embodiment, the present invention also provides a method for measuring the activity of a V2R agonist or antagonist or a method for screening for a V2R agonist or antagonist, comprising the following steps (A') to (C'):

(A') preparing a mixture containing a cell expressing V2R, a cAMP dependent calcium channel and a calcium sensitive protein, a luminescent substrate for the calcium sensitive protein, a $Ca^{2+}$-free medium and a test compound;

(B') adding a $Ca^{2+}$-containing solution to the mixture prepared in (A'); and (C') measuring the luminescence of the calcium sensitive protein emitted from the cell.

In this context, an appropriate amount of AVP is further added to the mixture of the step (A') in order to measure the activity of a V2R antagonist or screen for a V2R antagonist.

The materials used in the steps such as reagents or apparatuses and conditions for the steps can be prepared or set appropriately by those skilled in the art with reference to the description of "2. Cell expressing V2R, cAMP dependent calcium channel and calcium sensitive protein, and composition and kit comprising the cell" and the method provided by the present invention, comprising the steps (A)-(C).

On the basis of the amount of luminescence of the calcium sensitive protein obtained as a result of carrying out the method, those skilled in the art can appropriately quantify the V2R agonistic activity or V2R antagonistic activity of the test compound and can also determine the test compound as being a V2R agonist or a V2R antagonist or not.

In an alternative embodiment, the present invention also provides a method for measuring the activity of a V2R antagonist or a method for screening for a V2R antagonist, comprising the following steps (A") to (C"):

(A") preparing a mixture containing a cell expressing V2R, a cAMP dependent calcium channel and a calcium sensitive protein, a luminescent substrate for the calcium sensitive protein, a $Ca^{2+}$-containing medium, AVP and a test compound;

(B") adding forskolin to the mixture prepared in (A"); and (C") measuring the luminescence of the calcium sensitive protein emitted from the cell.

The materials used in the steps such as reagents or apparatuses and conditions for the steps can be prepared or set appropriately by those skilled in the art with reference to the description of "2. Cell expressing V2R, cAMP dependent calcium channel and calcium sensitive protein, and composition and kit comprising the cell" and the method provided by the present invention, comprising the steps (A)-(C).

This method utilizes the desensitization of the cAMP dependent calcium channel to detect the activity of a V2R antagonist. Specifically, when the test compound is a V2R antagonist, the binding of AVP to V2R is inhibited. In this state, the addition of forskolin that activates adenylate cyclase forms cAMP, which in turn activates the cAMP dependent calcium channel (e.g., CNG calcium). Thus, the calcium sensitive protein emits luminescence. However, if the test compound is not a V2R antagonist, AVP binds to V2R to form cAMP before addition of forskolin so that the cAMP dependent calcium channel (e.g., CNG calcium) is activated. In this state, the subsequent addition of forskolin desensitizes the once activated cAMP dependent calcium channel, which is no longer activated by the addition of forskolin. Thus, the calcium sensitive protein does not emit luminescence.

In one embodiment, the method provided by the present invention, comprising the steps (A") to (C"), is capable of accurately quantifying the inhibitory activity of a V2R antagonist in a high concentration range.

On the basis of the amount of luminescence of the calcium sensitive protein obtained as a result of carrying out the method, those skilled in the art can appropriately quantify the V2R antagonistic activity of a test compound and can also determine the test compound as being a V2R antagonist or not.

Since the V2R antagonist can be utilized as a hypotensive drug, a therapeutic drug for hyponatremia, a therapeutic drug for SIADH, or the like, a composition comprising the compound determined as a V2R antagonist as a result of carrying out the method can be prepared as a hypotensive agent, a therapeutic agent for hyponatremia or a therapeutic agent for SIADH.

5. Bioassay Method Using Cell Expressing GLP-1 Receptor, cAMP Dependent Calcium Channel and Calcium Sensitive Protein In one embodiment, the present invention provides a method for measuring the amount of an active form of GLP-1 in a biological sample, a method for determining a risk of developing a GLP-1-associated disease or a method for determining the effectiveness of treatment of a GLP-1-associated disease, comprising the following steps (A) to (C):

(A) preparing a mixture containing a cell expressing a GLP-1 receptor, a cAMP dependent calcium channel and a calcium sensitive protein, a luminescent substrate for the calcium sensitive protein, a $Ca^{2+}$-free medium and a biological sample derived from a test subject;

(B) adding a $Ca^{2+}$-containing solution to the mixture prepared in (A); and (C) measuring the luminescence of the calcium sensitive protein emitted from the cell.

The materials used in the steps such as reagents, apparatuses or biological samples and conditions for the steps can be prepared or set appropriately by those skilled in the art with reference to the description of "3. Cell expressing GLP-1 receptor, cAMP dependent calcium channel and calcium sensitive protein, and composition and kit comprising the cell" and "4. Bioassay method using cell expressing V2R, cAMP dependent calcium channel and calcium sensitive protein".

The order of addition of the substances described in the step (A) of the method can be set appropriately by those skilled in the art.

The present invention provides, for example, a method for measuring the amount of an active form of GLP-1 in a biological sample or a method for determining the effectiveness of treatment of a GLP-1-associated disease, comprising the following steps:

(1) seeding, into a plate for cell culture, a cell expressing a GLP-1 receptor, a cAMP dependent calcium channel and a calcium sensitive protein, the cell being suspended in a $Ca^{2+}$-free medium supplemented with a luminescent substrate for the calcium sensitive protein;

(2) adding a biological sample derived from a test subject to the cell and culturing the cell; and (3) adding a $CaCl_2$ solution to the cultured cell and measuring the luminescence of the calcium sensitive protein emitted from the cell.

The culture of the step (2) may be sterile culture, but does not have to be sterile. For example, when the incubation time of the step (2) is within 4 hours, sterile culture is not required for such a short time.

In the step (3), the luminescence is emitted by the calcium sensitive protein such as aequorin immediately after addition of the $CaCl_2$ solution and can be measured by a method which is well known by those skilled in the art. For example, a luminometer capable of automatically and continuously performing stirring and measurement (PerkinElmer Inc., ARVO-Sx) is used, and the amount of luminescence can be measured by integrating luminescence values for 15-30 seconds after stirring. The apparatus that can be used in the measurement of the amount of luminescence can be selected appropriately by those skilled in the art.

In one embodiment, the composition comprising the cell expressing a GLP-1 receptor, a cAMP dependent calcium channel and a calcium sensitive protein, provided by the present invention, is capable of detecting GLP-1, a GLP-1 receptor agonist or a GLP-1 receptor antagonist with high sensitivity.

Accordingly, in a preferable embodiment, the method provided by the present invention does not include the step of concentrating GLP-1, a GLP-1 receptor agonist or a GLP-1 receptor antagonist from a biological sample (e.g., the step of using columns (e.g., C18 columns such as Sep-Pak C18 columns), the step of using an ultrafiltration apparatus or the step of using a centrifugation concentration apparatus).

Furthermore, in one embodiment, the method provided by the present invention is capable of measuring the total amount of both the active form of GLP-1 (7-36) and the active form of GLP-1 (7-37) by a single operation.

Moreover, the present invention provides a method for measuring the activity of a GLP-1 receptor agonist or antagonist or a method for screening for a GLP-1 receptor agonist or antagonist, comprising the following steps (A') to (C'):

(A') preparing a mixture containing a cell expressing a GLP-1 receptor, a cAMP dependent calcium channel and a calcium sensitive protein, a luminescent substrate for the calcium sensitive protein, a calcium-free medium and a test compound;

(B') adding a calcium-containing solution to the mixture prepared in (A'); and (C') measuring the luminescence of the calcium sensitive protein emitted from the cell.

In this context, an appropriate amount of GLP-1 is further added to the mixture of the step (A') in order to measure the activity of a GLP-1 receptor antagonist or screen for a GLP-1 receptor antagonist.

The materials used in the steps such as reagents or apparatuses and conditions for the steps can be prepared or set appropriately by those skilled in the art with reference to the description of "3. Cell expressing GLP-1 receptor, cAMP dependent calcium channel and calcium sensitive protein, and composition and kit comprising the cell", "4. Bioassay method using cell expressing V2R, cAMP dependent calcium channel and calcium sensitive protein" and the method provided by the present invention, comprising the steps (A)-(C).

On the basis of the amount of luminescence of the calcium sensitive protein obtained as a result of carrying out the method, those skilled in the art can appropriately quantify the GLP-1 receptor agonistic activity or GLP-1 receptor antagonistic activity of the test compound and can also determine the test compound as being a GLP-1 receptor agonist or antagonist or not.

Since the GLP-1 receptor agonist can be utilized as a therapeutic drug for type 2 diabetes mellitus, a composition comprising the compound determined as a GLP-1 receptor agonist as a result of carrying out the method can be prepared as a therapeutic agent for type 2 diabetes mellitus.

In one embodiment, the present invention also provides a method for measuring the activity of a GLP-1 receptor antagonist or a method for screening for a GLP-1 receptor antagonist, comprising the following steps (A") to (C"):

(A") preparing a mixture containing a cell expressing a GLP-1 receptor, a cAMP dependent calcium channel and a calcium sensitive protein, a luminescent substrate for the calcium sensitive protein, a $Ca^{2+}$-containing medium, GLP-1 and a test compound;

(B") adding forskolin to the mixture prepared in (A"); and (C") measuring the luminescence of the calcium sensitive protein emitted from the cell.

The materials used in the steps such as reagents or apparatuses and conditions for the steps can be prepared or set appropriately by those skilled in the art with reference to the description of "3. Cell expressing GLP-1 receptor, cAMP dependent calcium channel and calcium sensitive protein, and composition and kit comprising the cell", "4. Bioassay method using cell expressing V2R, cAMP dependent calcium channel and calcium sensitive protein" and the method provided by the present invention, comprising the steps (A)-(C).

On the basis of the amount of luminescence of the calcium sensitive protein obtained as a result of carrying out the method, those skilled in the art can appropriately quantify the GLP-1 receptor antagonistic activity of the test compound and can also determine the test compound as being a GLP-1 receptor antagonist or not.

Hereinafter, the present invention will be further described with reference to Examples. However, the present invention is not limited to them.

EXAMPLES

A. Experiment on Cell Expressing V2R
1. Details on Method for Constructing Frozen Cell The cDNA sequence of human V2R (Genbank No. NM_001146151.1) (SEQ ID NO: 5) was amplified by the PCR method from a human-derived cDNA library and cloned into pUC18. The human vasopressin receptor isoform 2 (V2R) cDNA cloned in pUC18 was recloned into a pEF2 vector to prepare pEFhV2R.

Figure 13:
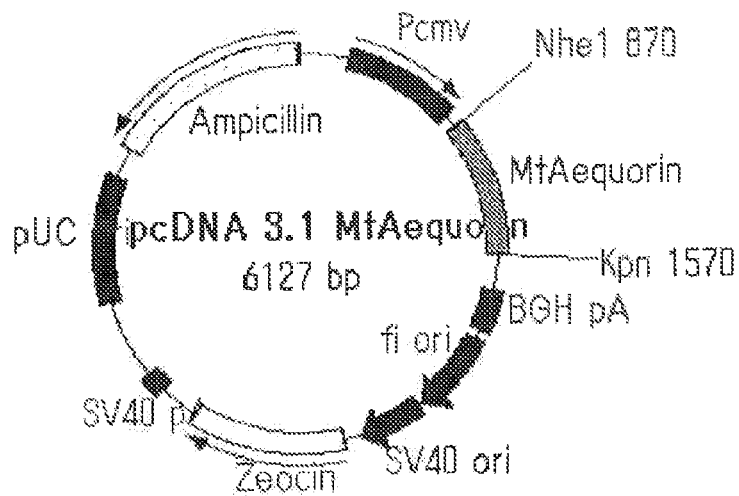
FIG. 13 shows a plasmid pcDNA mt s AEQ.
Figure 18:
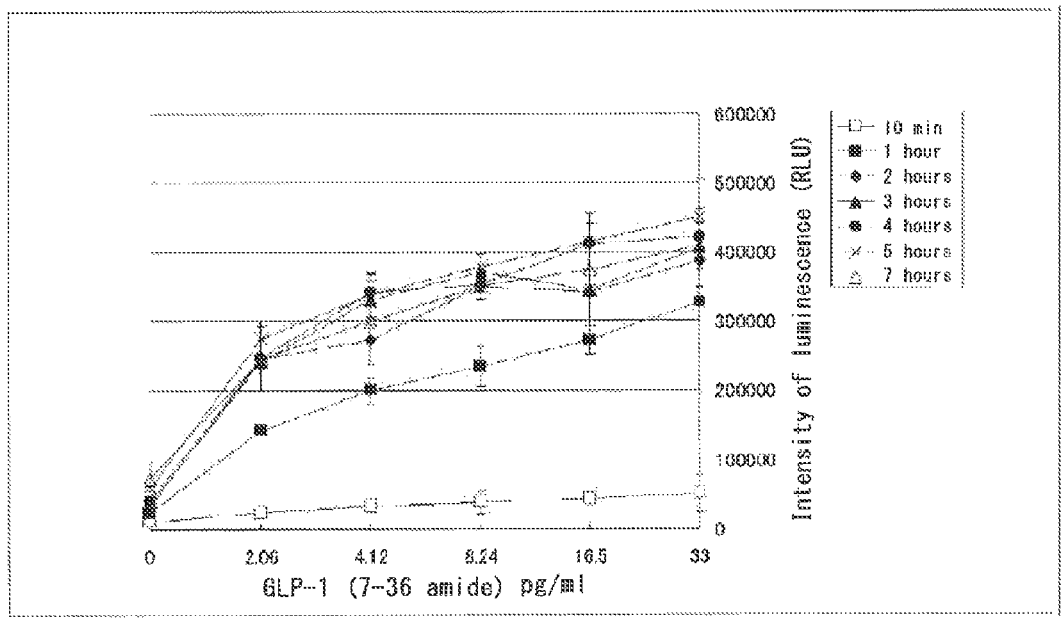
FIG. 18 shows effects of incubation time on an amount of luminescence emitted from CHO cell lines expressing human GLP-1 receptor, modified CNG channel and modified aequorin.

The cDNA sequence of a cyclic nucleotide dependent calcium channel (Genbank No. BC048775) (SEQ ID NO: 4) was amplified by the PCR method from a mouse olfactory epithelial cell-derived cDNA library (1994-bp) and cloned into an expression vector (pCMVSPORT, Invitrogen Corp.) to prepare pmCNGα2 (FIG. 18). Furthermore, for enhancing cAMP selectivity and sensitivity thereto, a construct pmCNGα2MW expressing a modified cyclic nucleotide dependent calcium channel (SEQ ID NO: 6) in which 460th cysteine (C) is substituted with tryptophan (W) and the 583rd glutamic acid (E) is substituted with methionine (M) was prepared by the point-mutation PCR method. Moreover, a synthetic apoaequorin cDNA sequence (676 bp) (SEQ ID NO: 7) that was optimized for human codon usage by the oligo DNA elongation method, and that has a mitochondrial targeting signal was treated with restriction enzymes KpnI and NheI and cloned into pcDNA3.1 (Invitrogen Corp.) treated with KpnI and NheI to prepare an aequorin expression vector pcDNA mt sAEQ (FIG. 13).

CHO cells were seeded at a cell density of $1.0 \times 10^5$ cells/ml into a 10-cm² Petri dish. On the next day, the cells were transfected with 1 μg of pEF2 V2R, 2 μg of pmCNGα2MW, and 2 μg of pcDNA mt sAEQ per Petri dish using FuGENE6™ (Roche Applied Science). On the next day, the cells were dissociated from the Petri dish by the addition of 400 μL of a Versene solution (EDTA) to the Petri dish and suspended in a DMEM/F12 medium containing 10 mL of 5% cFCS. The obtained suspension was centrifuged at 1000 rpm for 5 minutes. Then, the pellet was dissolved at a density of $2-5 \times 10^6$ cells/mL in 1 mL of CELLBANKER and stored at −80° C.

2. Concentration Dependent Curve and Lowest Detection Sensitivity of AVP Obtained Using Frozen Cell 1 ml ($3 \times 10^6$ cells/ml) of the frozen cells prepared in 1 was thawed in a warm bath and suspended in 10 mL of a washing buffer (calcium-free CO2-independent medium, Invitrogen Corp.). After centrifugation at 1000 rpm for 5 minutes, 12 mL of a culture buffer (5% PEG6000, calcium-free CO2-independent medium) was added to the obtained precipitate, and 6 μL of 4 mM ViviRen (Promega Corp.) was added thereto. The mixture was seeded at 50 μL/well into a 96-well plate. AVP serially diluted with a sample buffer was further added thereto (n=3) at 50 μL/well, and the cells were cultured at room temperature for 3 hours. 3 mM $CaCl_2$ solution was added thereto at 100 μL/well, and the amount of luminescence was measured using a luminometer (PerkinElmer Inc., ARVO-Sx; hereinafter, the same model was used in Examples). An AVP concentration dependent curve is shown in FIG. 1.

Figure 2:
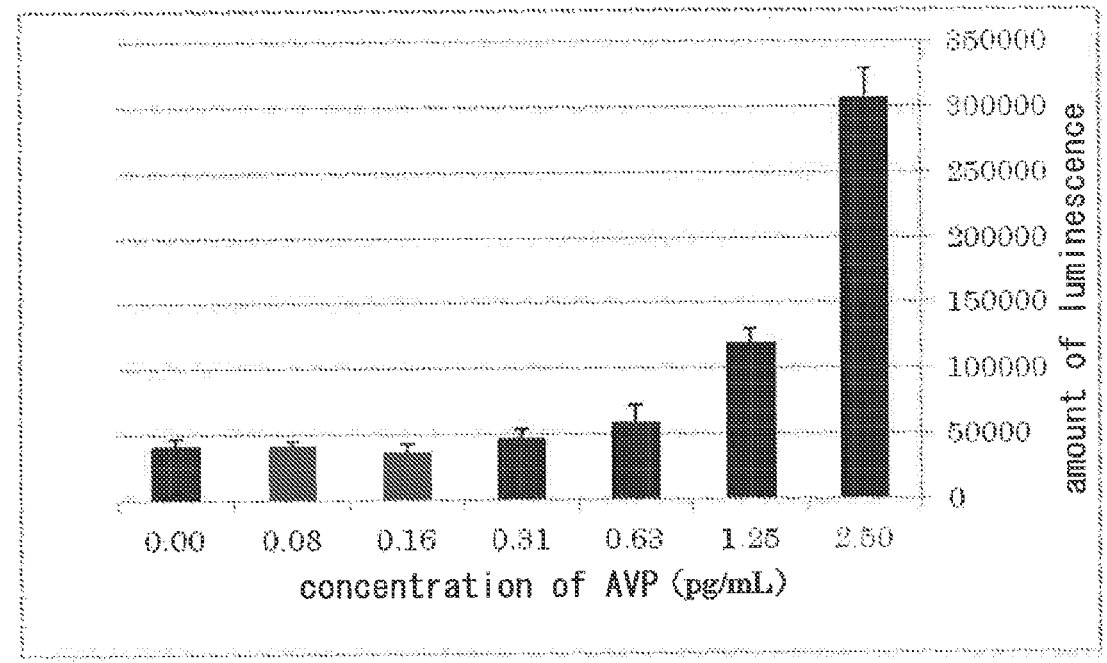
FIG. 2 shows an amount of luminescence emitted from the CHO cells expressing a human vasopressin receptor (human V2R), modified CNG channel and modified aequorin, in the presence of a low dose of AVP.

As shown in FIG. 2 (magnified view of the low concentration range), the minimum detectable quantity for AVP was 0.63 pg/mL so that the detected value was able to be significantly discriminated from the value which is calculated by blank value +3SD. Moreover, since aequorin performs luminescent reaction, a high signal to blank ratio (S/N ratio) (i.e., a 80 pg/mL of AVP, S/N ratio of approximately 56 times (3194263/56805)) was obtained by the method of the present invention.

Figure 3:
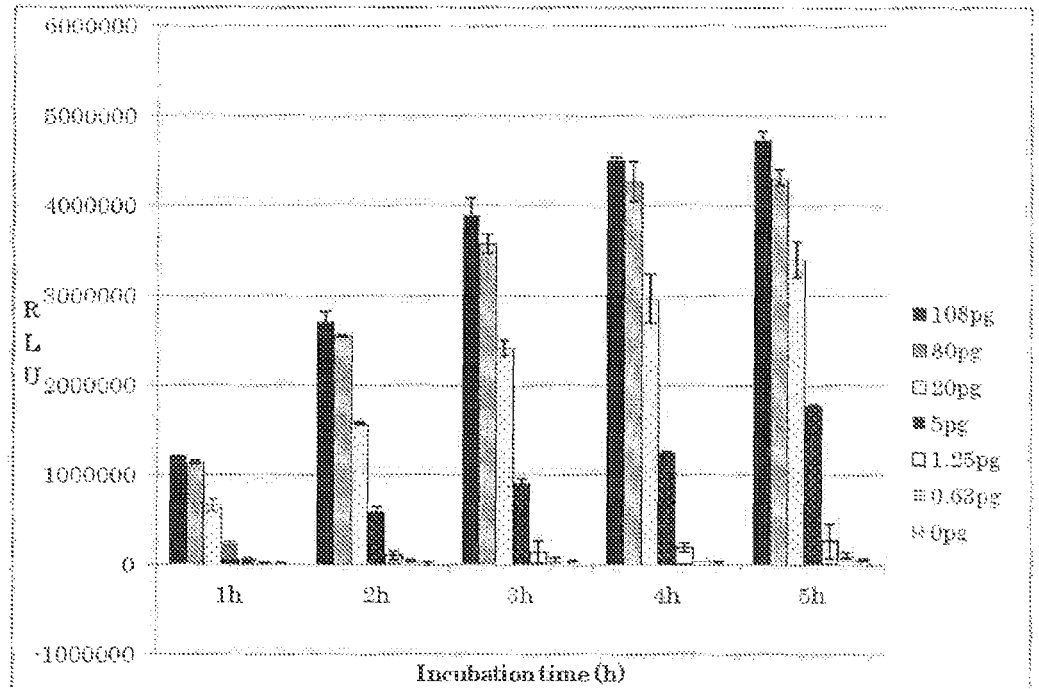
FIG. 3 shows effects of the incubation time on an amount of luminescence emitted from the CHO cells expressing human V2R, modified CNG channel and modified aequorin.

4. Study on Incubation Time after Addition of Substrate (ViviRen) for Aequorin Luminescence 1 ml ($3 \times 10^6$ cells/ml) of the frozen cells prepared in 1 was thawed in a warm bath and suspended in 12 mL of a washing buffer. After centrifugation at 1000 rpm for 5 minutes, 12 mL of a culture buffer was added to the obtained precipitate, and 6 μL of 4 mM ViviRen was added thereto. The mixture was seeded at 50 μL/well into a 96-well plate. AVP serially diluted with a culture buffer was added thereto at 50 μL/well. After 1, 2, 3, 4, or 5 hours, 3 mM $CaCl_2$ solution was added thereto at 100 μL/well, and the amount of luminescence was measured using a luminometer. It was demonstrated that the amount of luminescence reached a plateau at 4 hours after ViviRen addition (see FIG. 3).

5. Study on Amount of Receptor Plasmid Used in Transfection 10 mL of CHO cells having a density of $1 \times 10^5$ cells/mL was seeded into a 10-cm² Petri dish and cultured for 1 day. Then, 3 ug of pcDNA mt sAEQ, 1 ug of pmCNGα2MW, and 0 to 1 ug of pEF2 V2R plasmid were mixed and further mixed with 600 μL of DMEM/F12 and 18 μL of FuGENE6 (Roche Applied Science), and transfection was performed. After further overnight culture, the medium was removed, and the cells were washed with 10 mL of PBS. Then, 800 μL of Versene was added thereto, and the cells were cultured at 37° C. for 5 minutes and then suspended in 10 mL of a washing buffer. After centrifugation at 1000 rpm for 5 minutes, the precipitate was dissolved in 12 mL of a culture buffer, and 6.5 μL of 4 mM ViviRen was added thereto. The cell suspension was seeded at 50 μL/well into a 96-well plate supplemented with 50 μL/well of a concentration series of AVP. After culture at room temperature for 3 hours, 3 mM $CaCl_2$ solution was added thereto at 100 μL/well, and the amount of luminescence was measured using a luminometer.

Figure 4:
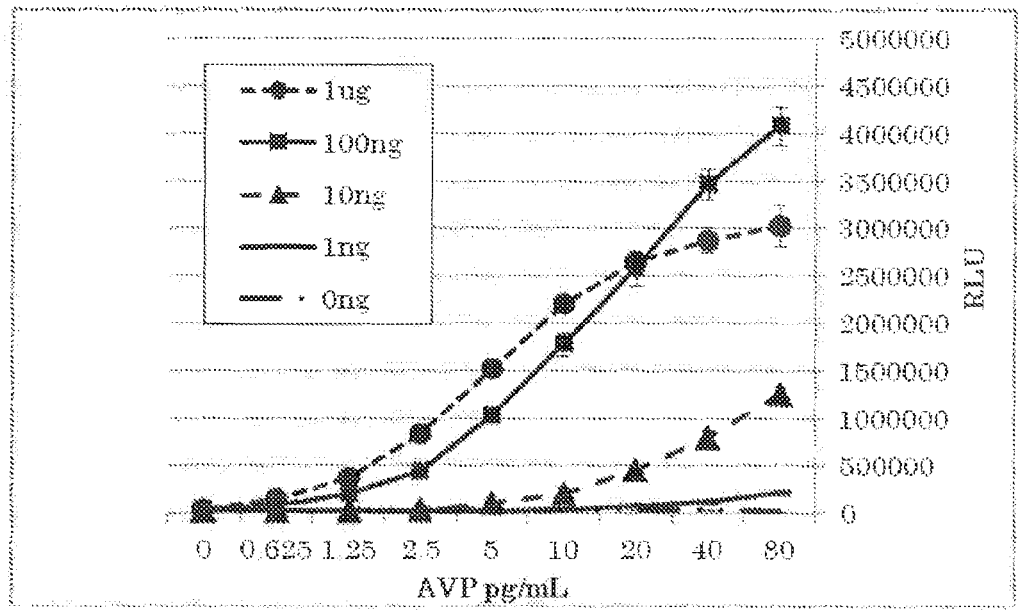
FIG. 4 shows effects of an amount of introduced V2R expression plasmid on an amount of luminescence emitted from the CHO cells expressing human V2R, modified CNG channel and modified aequorin.

It was demonstrated that the receptor plasmid in an amount of 1 ug/plate in transfection was required for obtaining the optimum amount of luminescence (see FIG. 4).

6. Optimization of Cell Density 1 ml ($3 \times 10^6$ cells/ml) of the frozen cells prepared in 1 was thawed in a warm bath and suspended in 10 mL of a sample buffer. After centrifugation at 1000 rpm for 5 minutes, 10 mL of a sample buffer was added to the obtained precipitate. A cell series whose cell density was adjusted to densities $1.0 \times 10^5$ cells/mL to $2 \times 10^6$ cells/mL was prepared. The cells were suspended by the addition of 6 μL of 4 mM ViviRen. The cell suspension was seeded into a 96-well plate supplemented with 50 μL/well of AVP serially diluted with a culture buffer. After culture for 3 hours, 3 mM $CaCl_2$ solution was added thereto at 100 μL/well, and the amount of luminescence was measured using a luminometer.

Figure 5:
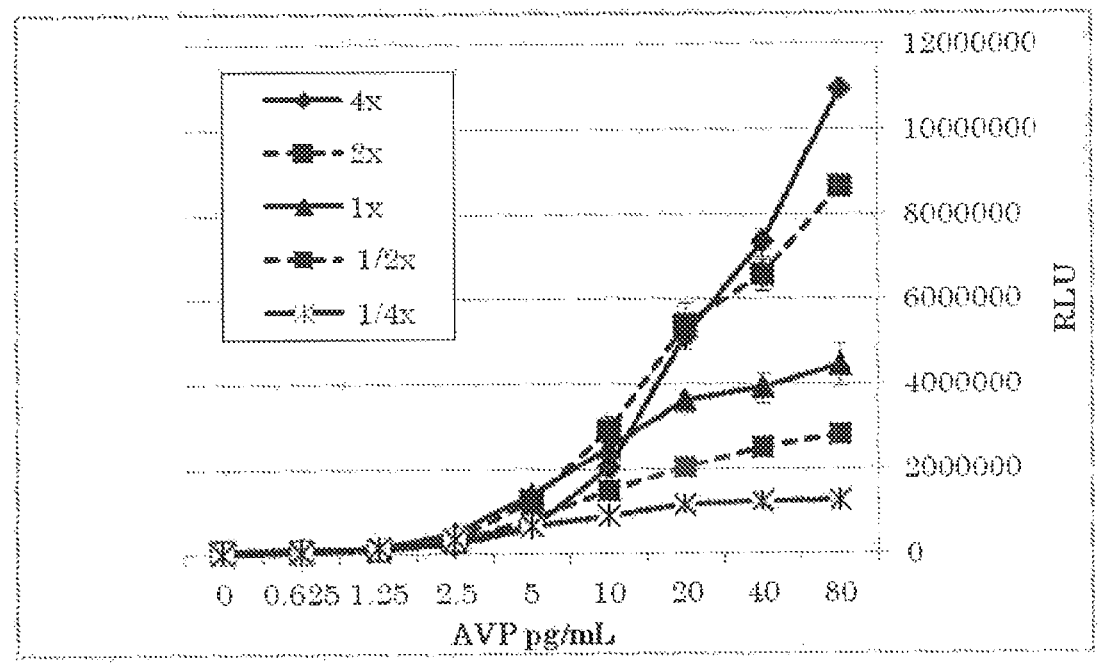
FIG. 5 shows a relationship between a density of CHO cells expressing human V2R, modified CNG channel and modified aequorin, and an amount of luminescence from the cells.
Figure 6:
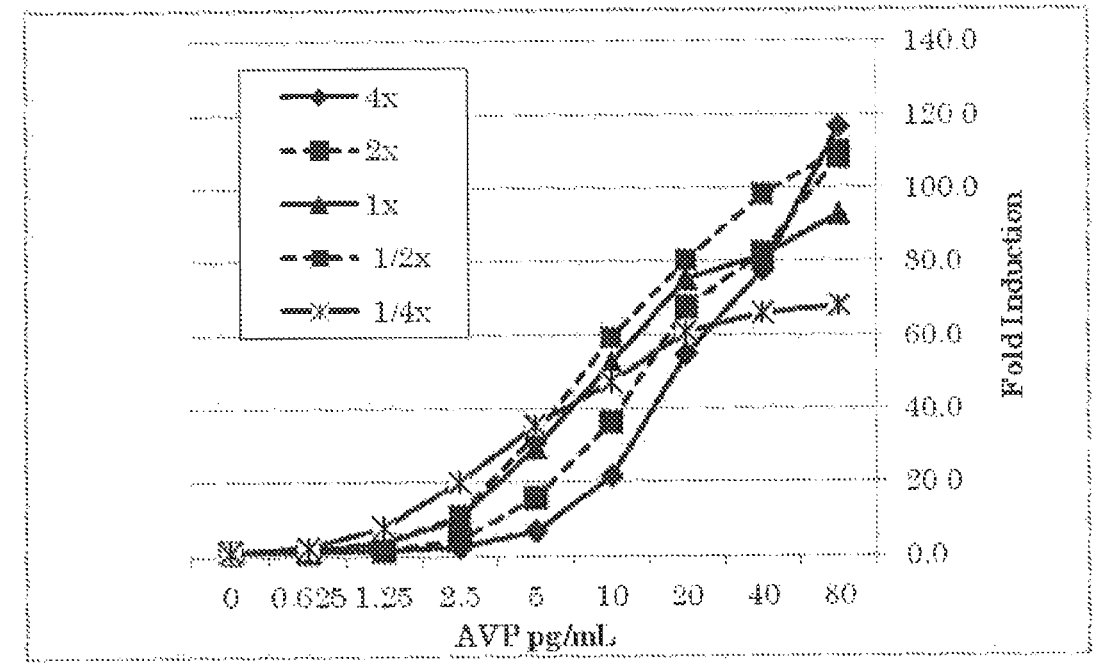
FIG. 6 shows a relationship between a density of CHO cells expressing human V2R, modified CNG channel and modified aequorin, and an amount of luminescence from the cells, where the amount of luminescence is indicated as a relative value which is calculated on the assumption that a relative value for each blank is 1.

As shown in FIGS. 5 and 6, the amount of luminescence was increased in a cell density dependent manner.

7. Study on Concentration of Added $CaCl_2$ Detection Solution 1 ml ($3\times10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 μL of 4 mM ViviRen was added thereto. The mixture was seeded at 50 μL/well into a 96-well plate. AVP serially diluted with a culture buffer was added thereto at 50 μL/well, and the cells were cultured for 3 hours. Then, a $CaCl_2$ detection solution (final concentrations: 0 to 30 mM) was added thereto at 100 μL/well, and the amount of luminescence was measured using a luminometer.

Figure 7:
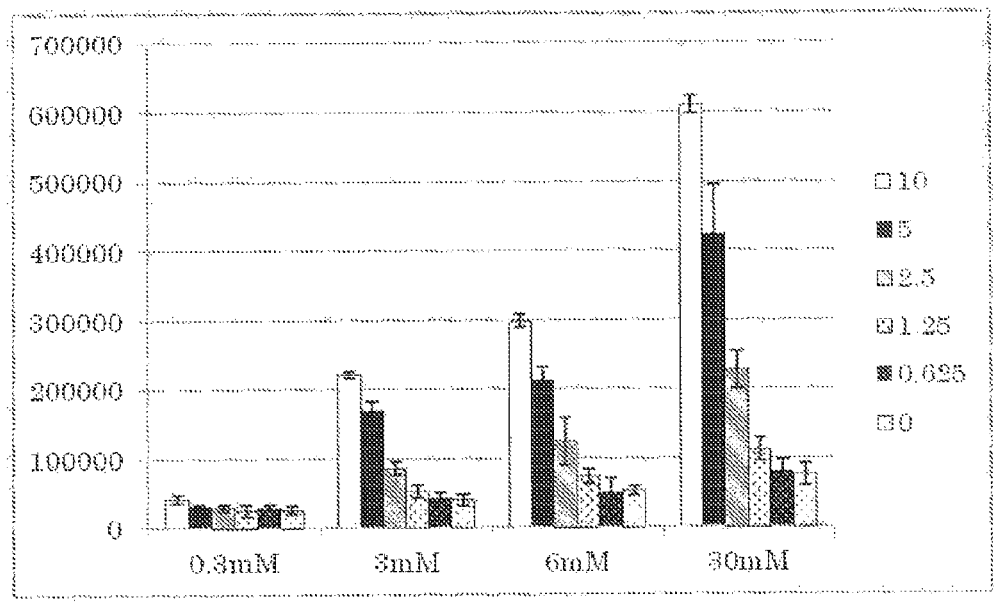
FIG. 7 shows effects of a concentration of added $CaCl_2$ on an amount of luminescence emitted from the CHO cells expressing human V2R, modified CNG channel and modified aequorin.

It was demonstrated that the optimum $CaCl_2$ concentrations were 30 mM at which a low value at background (0) and the high amount of luminescence in the sample were obtained (see FIG. 7).

8. Study on Dilution Linearity Using AVP Solution 1 ml ($3\times10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 μL of 4 mM ViviRen was added thereto. The mixture was seeded at 50 μL/well into a 96-well plate. The cells were cultured for 3 hours with an AVP solution diluted ½, ¼, ⅛, 1/16, or 1/32-fold with a sample buffer.

After the culture for 3 hours, 3 mM $CaCl_2$ solution was added thereto at 100 μL/well, and the amount of luminescence was measured using a luminometer.

Figure 8:
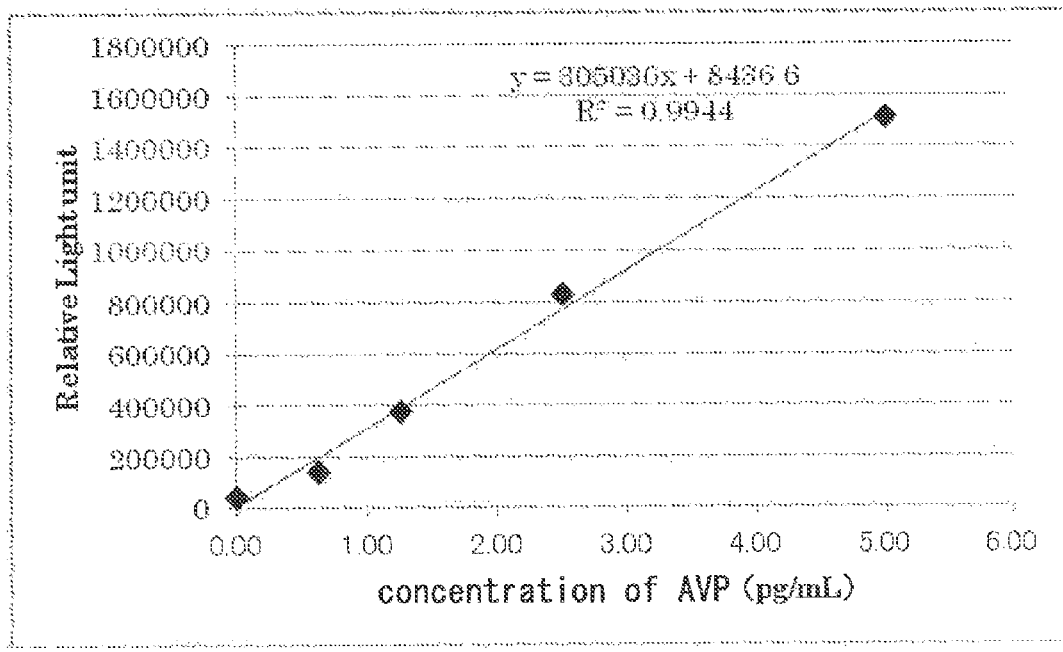
FIG. 8 shows that a kit provided by the present invention is capable of quantifying AVP.

As shown in FIG. 8, it was confirmed that the amount of luminescence was increased with linearity.

11. Sensitivity Comparison with Existing Kit Using AVP Solution 1 ml ($3\times10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 μL of 4 mM ViviRen was added thereto. The mixture was seeded at 50 μL/well into a 96-well plate. The cells were cultured for 3 hours with an AVP solution diluted ½, ¼, ⅛, 1/16, or 1/32-fold with a sample buffer.

Figure 9:
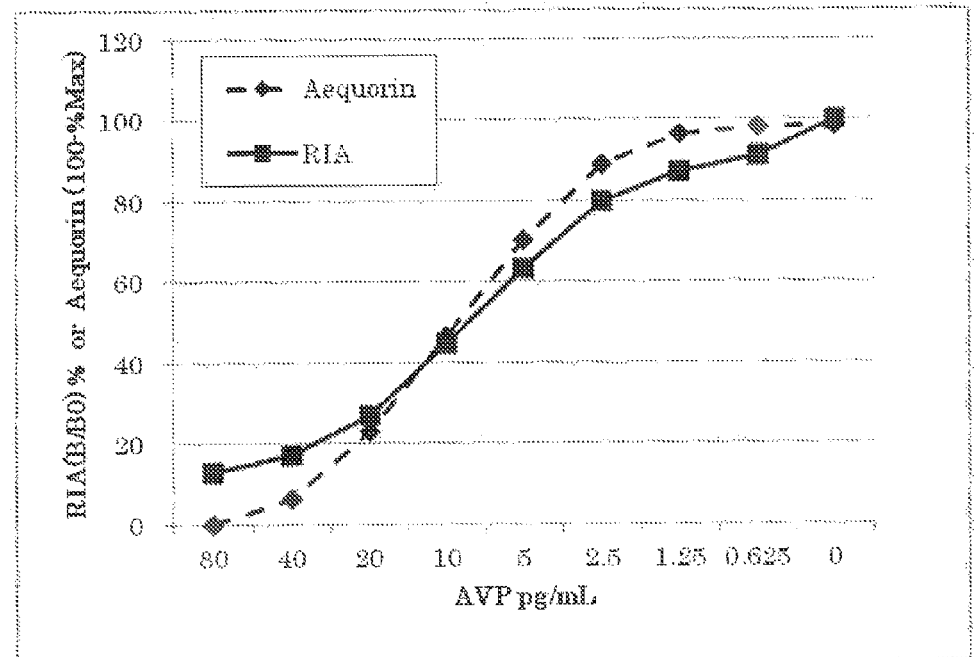
FIG. 9 shows the comparison of measurement ranges between a kit provided by the present invention and an AVP kit using radioimmunoassay.
Figure 10:
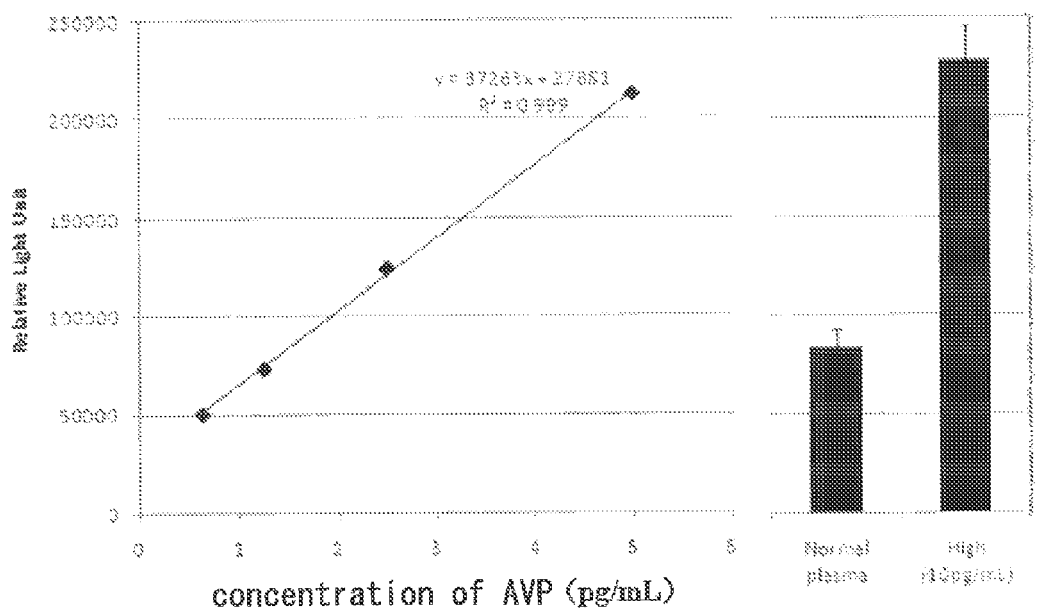
FIG. 10 shows the assay of normal individual plasma and plasma with a high AVP level using a kit provided by the present invention.

Values separately measured using the existing Mitsubishi Chemical Medience AVP-RIA kit are also shown. The values obtained using the RIA kit are indicated by a competitive inhibition rate (B/B0%) against radiolabeled AVP. Thus, for comparison, values calculated according to the equation 100−(amount of luminescence at each concentration/the maximum amount of luminescence)*100 are shown. The kit of the present invention was confirmed to maintain linearity even at a dose of 20 pg/mL or higher and have excellent sensitivity, compared with the existing RIA kit (see FIG. 9).

12. Study Using Human Clinical Sample 1 ml ($3\times10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 μL of 4 mM ViviRen was added thereto. The mixture was seeded at 50 μL/well into a 96-well plate. A dilution series of AVP serving as a standard solution, normal individual plasma, and plasma with a high AVP level prepared by the addition of AVP were used. 80 μL of a sample was diluted by the addition of 320 μL of a culture buffer and added to the plate at 50 μL/well, and the cells were cultured for 3 hours. 3 mM $CaCl_2$ solution was added thereto at 100 μL/well, and the amount of luminescence was measured using a luminometer.

Figure 11:
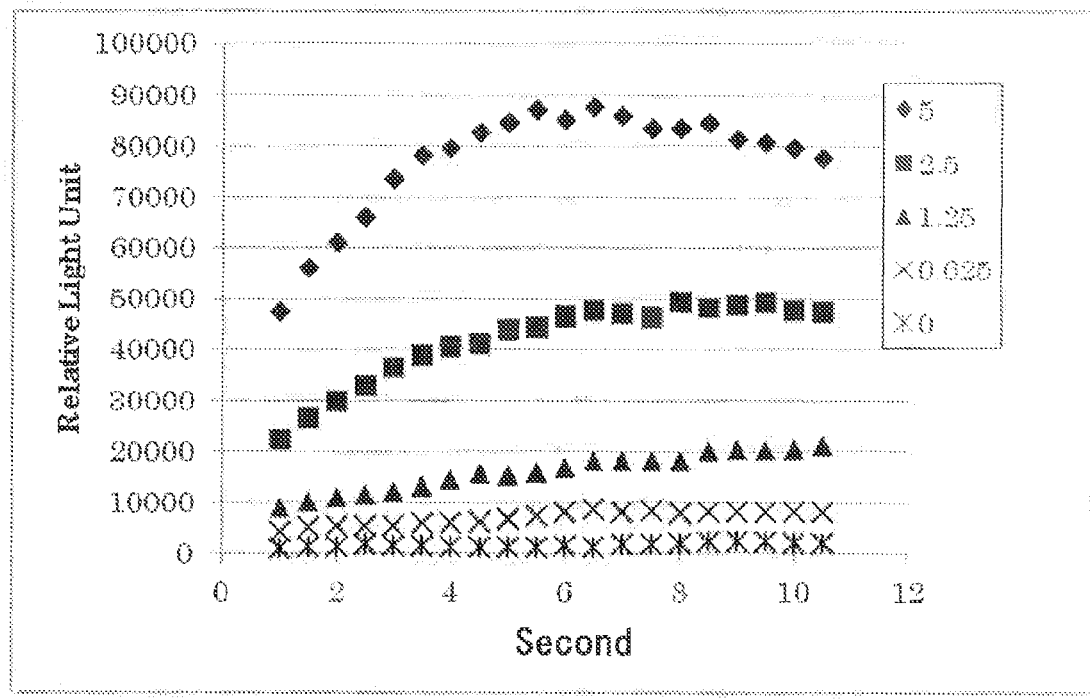
FIG. 11 shows the time course of an amount of luminescence emitted from the CHO cells expressing human V2R, modified CNG channel and modified aequorin. Time-dependent change in the amount of luminescence is shown for 0 to 5 pg/mL AVP.
Figure 12:
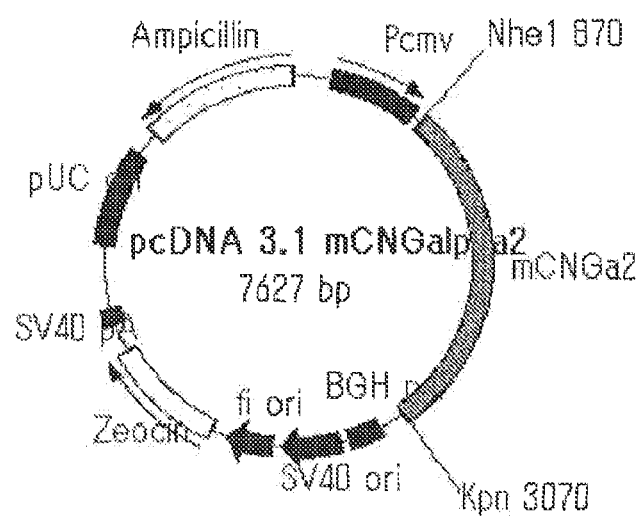
FIG. 12 shows a plasmid pmCNGα2.

13. Study on Time-dependent Change in Luminescence Using Kit Using Frozen Cell 1 ml ($3\times10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 μL of 4 mM ViviRen was added thereto. The mixture was seeded at 50 μL/well into a 96-well plate. AVP serially diluted with a culture buffer was added thereto at 50 μL/well, and the cells were cultured for 3 hours. 3 mM $CaCl_2$ solution was added thereto at 100 μL/well and stirred for 3 seconds. Then, the amount of luminescence was measured over time for 12 seconds using a luminometer. As a result, as shown in FIG. 11, relatively stable luminescence was observed as soon as the $CaCl_2$ solution was added.

Figure 14:
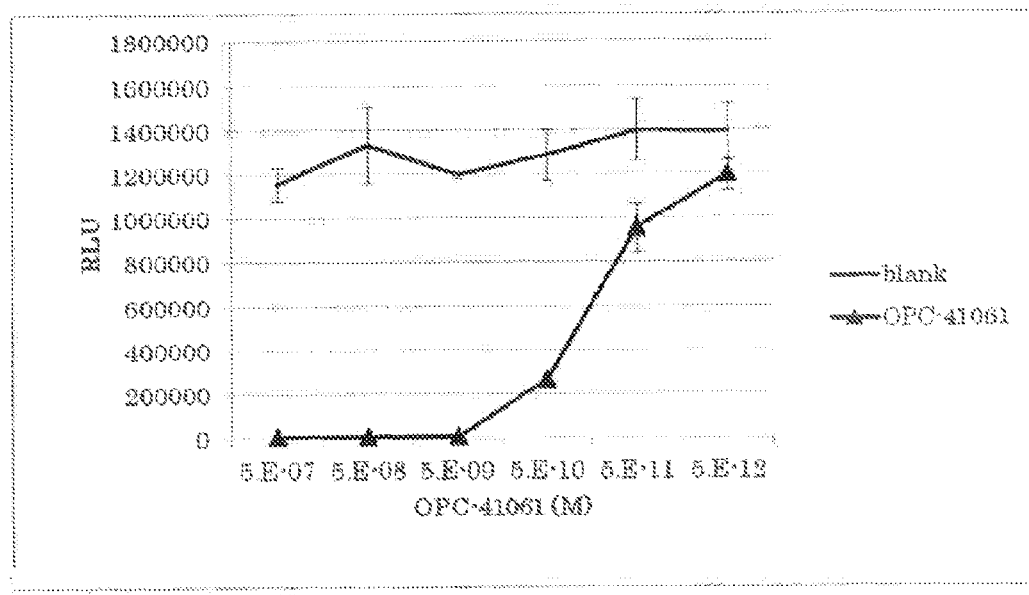
FIG. 14 shows a concentration of a compound and an amount of luminescence after culture of cells with a vasopressin antagonist (OPC-41061) in a calcium-containing medium and subsequent addition of $10^{-7}$ M AVP.
Figure 15:
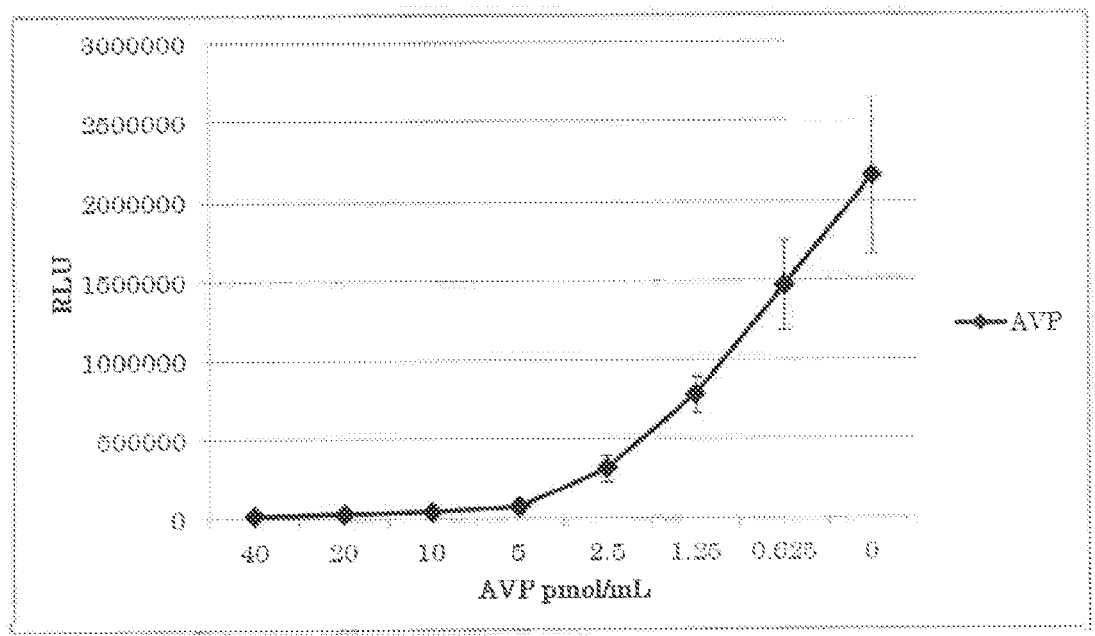
FIG. 15 shows a concentration of AVP and an amount of luminescence after culture of cells with each concentration of AVP in a calcium-containing medium and subsequent addition of $10^{-7}$ M (constant concentration) AVP.
Figure 16:
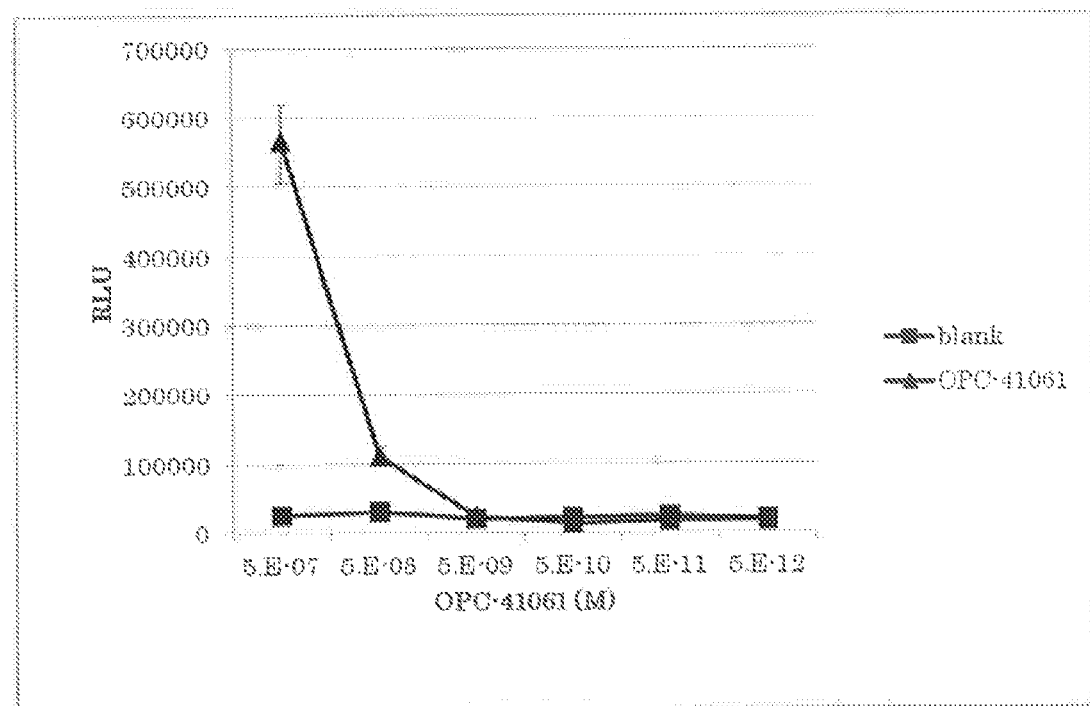
FIG. 16 shows a concentration of a compound and an amount of luminescence after culture of cells with a vasopressin antagonist (OPC-41061) in a calcium-containing medium, subsequent addition of $10^{-7}$ M AVP and further addition of $10^{-4}$ M forskolin.

14. Study on Detection of AVP and V2R Antagonist by Desensitization 1 ml ($3\times10^6$ cells/ml) of the frozen cells prepared in 1 was thawed in a warm bath and suspended in 10 mL of a washing buffer. The suspension was centrifuged at 1000 rpm for 5 minutes. 12 mL of a culture buffer was added to the obtained precipitate, and 6 μL of 4 mM ViviRen was added thereto. The mixture was seeded at 50 μL/well into a 96-well plate. AVP serially diluted with a calcium-containing culture buffer, and OPC-41061 were added thereto at 50 μL/well, and the cells were cultured for 3 hours. $10^{-7}$ M AVP was added thereto at 50 μL/well, and the amount of luminescence was measured using a luminometer (FIGS. 14 and 15). The vasopressin antagonist OPC-41061 inhibited the action of added AVP in a concentration dependent manner (FIG. 14). Moreover, when AVP and the cells were reacted in a calcium-containing medium, the re-addition of AVP did not cause luminescence due to the reaction that once occurred in the presence of a high concentration of AVP. The desensitization decreased an amount of luminescence in a concentration dependent manner of added AVP (FIG. 15). It was demonstrated that AVP can also be quantified by desensitization. Subsequently, $10^{-4}$ M forskolin was further added thereto at 50 μL/well, and the amount of luminescence was measured using a luminometer (FIG. 16). Only when the vasopressin antagonist inhibited the action of added AVP, the luminescence of forskolin was detected in a concentration dependent manner. Thus, it was demonstrated that a vasopressin antagonist can be detected by desensitization.

B. Experiment on Cell Expressing GLP-1 Receptor

1. Details on Method for Constructing Frozen Cell

The cDNA sequence of human GLP-1 receptor (Genbank No. BC113493) (SEQ ID NO: 9) was amplified by the PCR method from a human-derived cDNA library and cloned into pUC18. The human GLP-1 receptor (GLP-1R) cDNA cloned in pUC18 was recloned into a pCIneo vector to prepare pCIneoGLP-1R.

The cDNA sequence of a cyclic nucleotide dependent calcium channel (Genbank No. BC048775) was amplified by the PCR method from a mouse olfactory epithelial cell-derived cDNA library (1994-bp) and cloned into an expression vector (pCMVSPORT, Invitrogen Corp.) to prepare pmCNGα2. Furthermore, for enhancing cAMP selectivity and sensitivity thereto, a construct pmCNGα2MW expressing a modified cyclic nucleotide dependent calcium channel in which the 460th cysteine (C) is substituted with tryptophan (W) and the 583rd glutamic acid (E) is substituted with methionine (M) was prepared by the point-mutation PCR method. Moreover, a synthetic apoaequorin cDNA sequence (676 bp) that was optimized for human codon usage by the oligo DNA elongation method, and that has a mitochondrial targeting signal was treated with restriction enzymes KpnI and NheI and cloned into pcDNA3.1 (Invitrogen Corp.) treated with KpnI and NheI to prepare an aequorin expression vector pcDNA mt sAEQ.

CHO cell lines were seeded at a cell density of $1.0 \times 10^5$ cells/ml into a 10-cm² Petri dish. On the next day, the cells were transfected with 0.1 g of pCIneoGLP-1R, 1 µg of pmCNGα2MW, and 4 µg of pcDNA mt sAEQ per Petri dish using FuGENE6™ (Roche Applied Science). On the next day, the cells were dissociated from the Petri dish by the addition of 400 µL of a Versene solution (EDTA) to the Petri dish and suspended in a DMEM/F12 medium containing 10 mL of 5% cFCS. The obtained suspension was centrifuged at 1000 rpm for 5 minutes. Then, the pellet was dissolved at a density of $2-5 \times 10^6$ cells/mL in 1 mL of CELLBANKER and stored at $-80°$ C.

Figure 17:
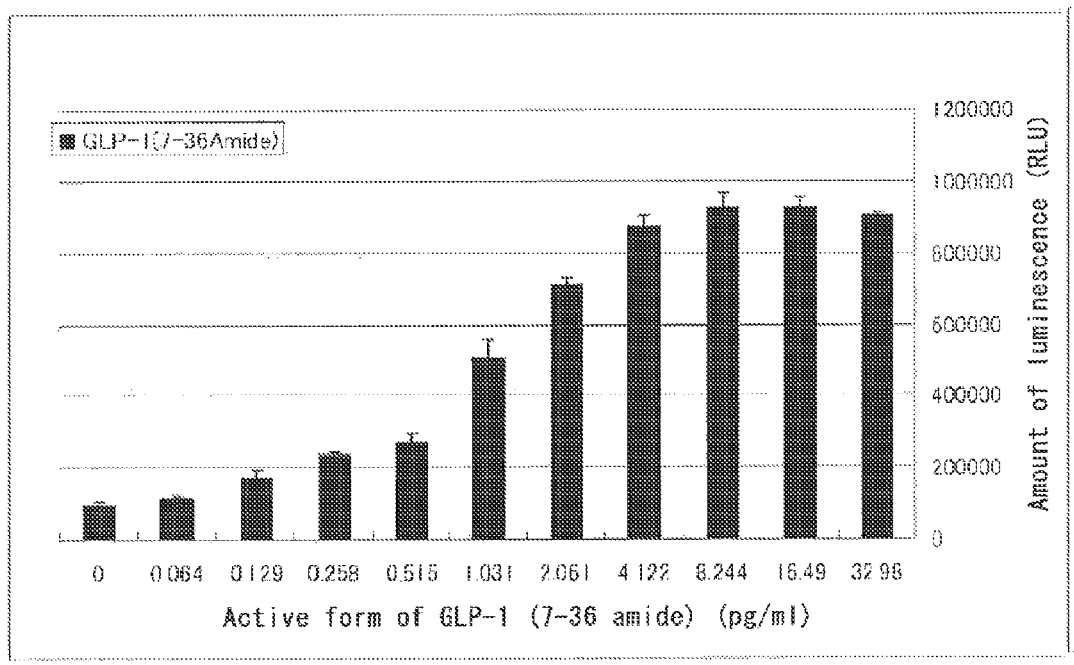
FIG. 17 shows that luminescence emitted from CHO cell lines expressing human GLP-1 receptor, modified CNG channel and modified aequorin is dependent on a concentration of an active form of GLP-1.

2. Concentration Dependent Curve and Lowest Detection Sensitivity of GLP-1 Obtained Using Frozen Cell 1 ml ($3 \times 10^6$ cells/ml) of the frozen cells prepared in 1 was thawed in a warm bath and suspended in 10 mL of a washing buffer (calcium-free CO2-independent medium, Invitrogen Corp.). After centrifugation at 1000 rpm for 5 minutes, 12 mL of a culture buffer (5% PEG6000, calcium-free CO2-independent medium) was added to the obtained precipitate, and 6 µL of 4 mM ViviRen (Promega Corp.) was added thereto. The mixture was seeded at 90 µL/well into a 96-well plate. The active form of GLP-1 (7-36 amide) serially diluted with a sample buffer was further added thereto (n=3) at 10 µL/well, and the cells were cultured at room temperature for 3 hours. 100 mM $CaCl_2$ solution was added thereto at 50 µL/well, and the amount of luminescence was measured using a luminometer (PerkinElmer Inc., ARVO-Sx; hereinafter, the same model was used in Examples). A concentration dependent curve of the active form of GLP-1 is shown in FIG. 17.

The minimum detectable quantity for the active form of GLP-1 was 0.078 pg/mL so that the detected value was able to be significantly discriminated from the value which is calculated by blank value +3SD. Moreover, since aequorin performs luminescent reaction, a high signal to blank ratio (S/N ratio) (i.e., a 33 pg/mL of active form of GLP-1, S/N ratio of approximately 9.3 times (902623/96686)) was obtained by the method of the present invention.

3. Study on Incubation Time after Addition of Substrate (ViviRen) for Aequorin Luminescence 1 ml ($3 \times 10^6$ cells/ml) of the frozen cells prepared in 1 was thawed in a warm bath and suspended in 12 mL of a washing buffer. After centrifugation at 1000 rpm for 5 minutes, 12 mL of a culture buffer was added to the obtained precipitate, and 6 µL of 4 mM ViviRen was added thereto. The mixture was seeded at 90 µL/well into a 96-well plate. The active form of GLP-1 serially diluted with a culture buffer was added thereto at 10 µL/well. After 0, 1, 2, 3, 4, 5 or 7 hours, 100 mM $CaCl_2$ solution was added thereto at 50 µL/well, and the amount of luminescence was measured using a luminometer. It was demonstrated that the amount of luminescence reached a plateau at 3 hours after ViviRen addition (see FIG. 18).

4. Study on Amount of Receptor Plasmid Used in Transfection 10 mL of CHO cells having a density of $0.7 \times 10^5$ cells/mL was seeded into a 10-cm² Petri dish and cultured for 1 day. Then, 4 ug of pcDNA mt sAEQ, 1 ug of pmCNGα2MW, and 0 to 1 ug of pCIneoGLP-1 receptor plasmid were mixed and further mixed with 600 µL of DMEM/F12 and 18 µL of FuGENE6 (Roche Applied Science), and transfection was performed. After further overnight culture, the medium was removed, and the cells were washed with 10 mL of PBS. Then, 800 µL of Versene was added thereto, and the cells were cultured at 37° C. for 5 minutes and then suspended in 10 mL of a washing buffer. After centrifugation at 1000 rpm for 5 minutes, the precipitate was dissolved in 12 mL of a culture buffer, and 6 µL of 4 mM ViviRen was added thereto. The cell suspension was seeded at 90 µL/well into a 96-well plate supplemented with 10 µL/well of a concentration series of GLP-1. After culture at room temperature for 3 hours, 100 mM $CaCl_2$ solution was added thereto at 50 µL/well, and the amount of luminescence was measured using a luminometer.

Figure 19:
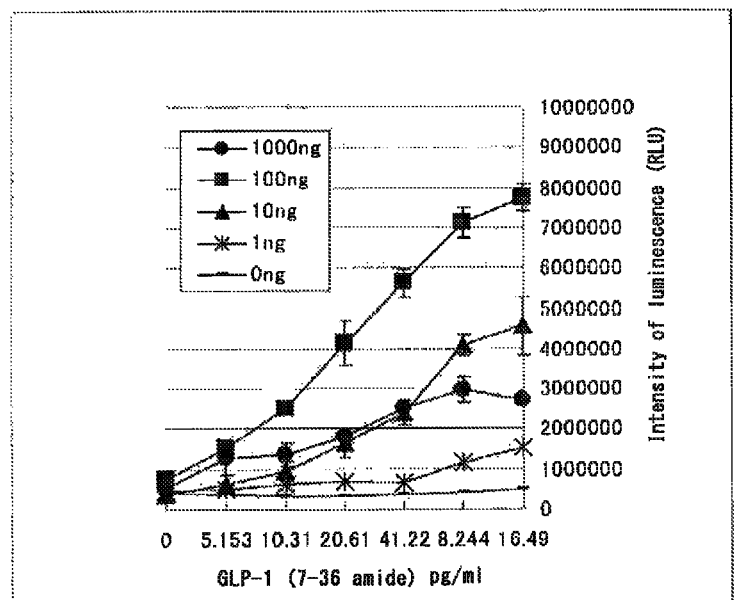
FIG. 19 shows effects of an amount of introduced GLP-1 receptor expression plasmid on an amount of luminescence emitted from CHO cell lines expressing human GLP-1 receptor, modified CNG channel and modified aequorin.

It was demonstrated that the receptor plasmid in an amount of 0.1 ug/plate in transfection was required for obtaining the optimum amount of luminescence (see FIG. 19).

5. Optimization of Cell Density 1 ml ($3 \times 10^6$ cells/ml) of the frozen cells prepared in 1 was thawed in a warm bath and suspended in 10 mL of a sample buffer. After centrifugation at 1000 rpm for 5 minutes, 10 mL of a sample buffer was added to the obtained precipitate. A cell series whose cell density was adjusted to densities $1.25 \times 10^5$ cells/mL to $1 \times 10^6$ cells/mL was prepared. The cells were suspended by the addition of 6 µL of 4 mM ViviRen. The cell suspension was seeded into a 96-well plate supplemented with 50 µL/well of GLP-1 serially diluted with a culture buffer. After culture for 3 hours, 100 mM $CaCl_2$ solution was added thereto at 100 µL/well, and the amount of luminescence was measured using a luminometer.

Figure 20:
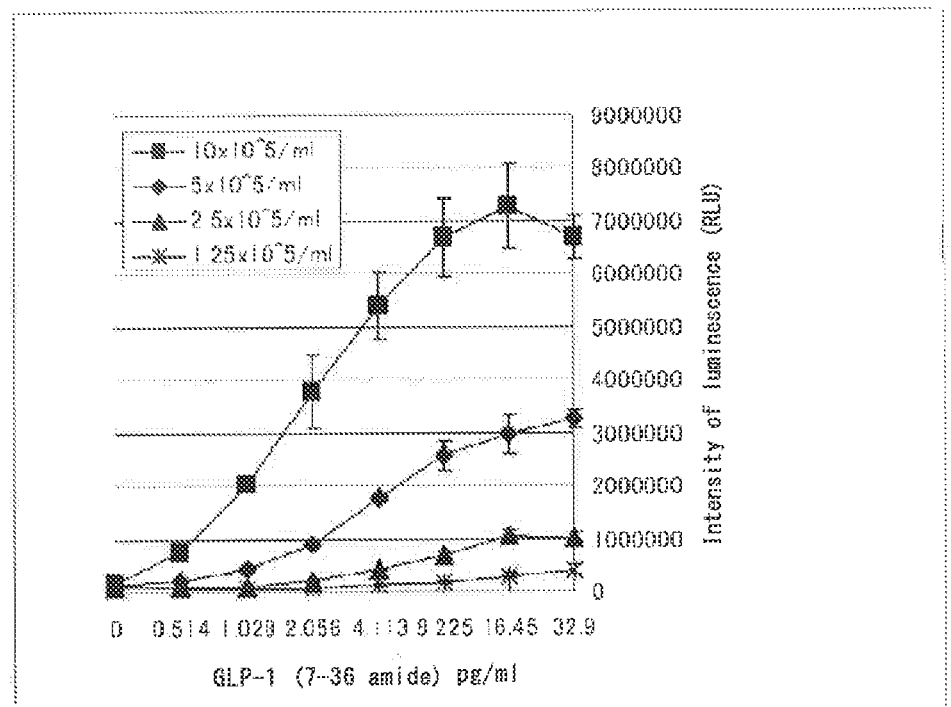
FIG. 20 shows a relationship between a density of CHO cell lines expressing human GLP-1 receptor, modified CNG channel and modified aequorin, and an amount of luminescence from the cells.
Figure 21:
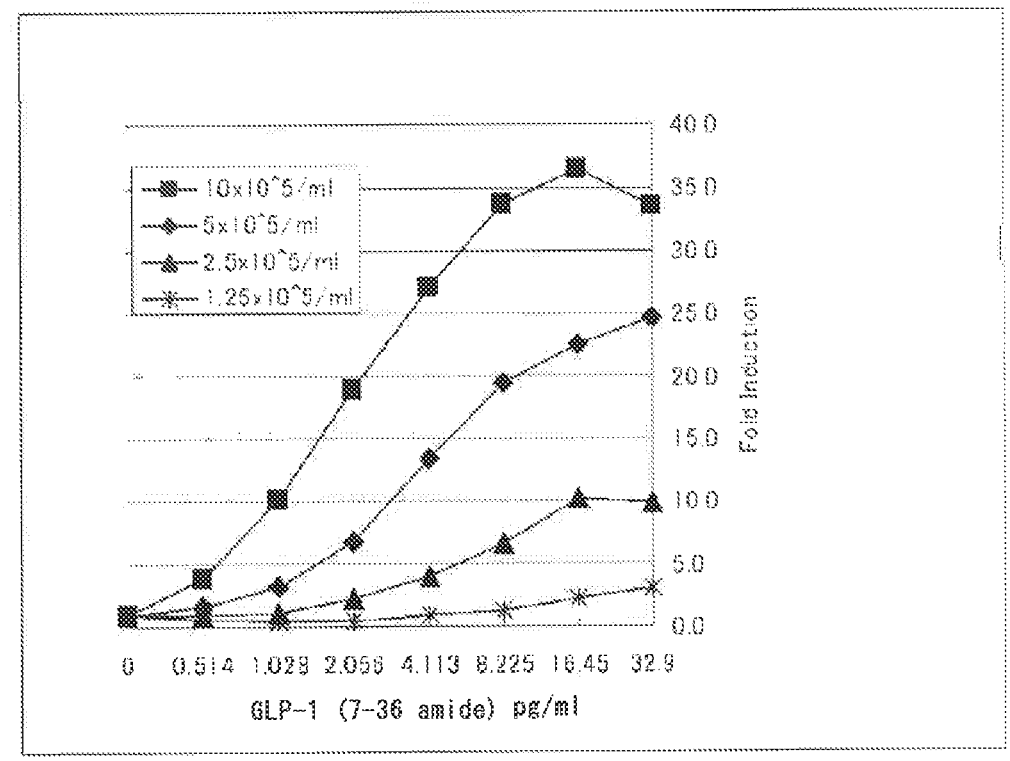
FIG. 21 shows a relationship between a density of CHO cell lines expressing human GLP-1 receptor, modified CNG channel and modified aequorin, and an amount of luminescence from the cells, where the amount of luminescence is indicated as a relative value which is calculated on the assumption that a relative value for each blank is 1.

As shown in FIGS. 20 and 21, the amount of luminescence was increased in a cell density dependent manner.

6. Study on Dilution Linearity Using GLP-1 Solution 1 ml ($3 \times 10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 µL of 4 mM ViviRen was added thereto. The mixture was seeded at 50 µL/well into a 96-well plate. The cells were cultured for 3 hours with a GLP-1 solution diluted ½, ¼, ⅛, 1/16, or 1/32-fold with a sample buffer.

After the culture for 3 hours, 100 mM $CaCl_2$ solution was added thereto at 50 µL/well, and the amount of luminescence was measured using a luminometer.

Figure 22:
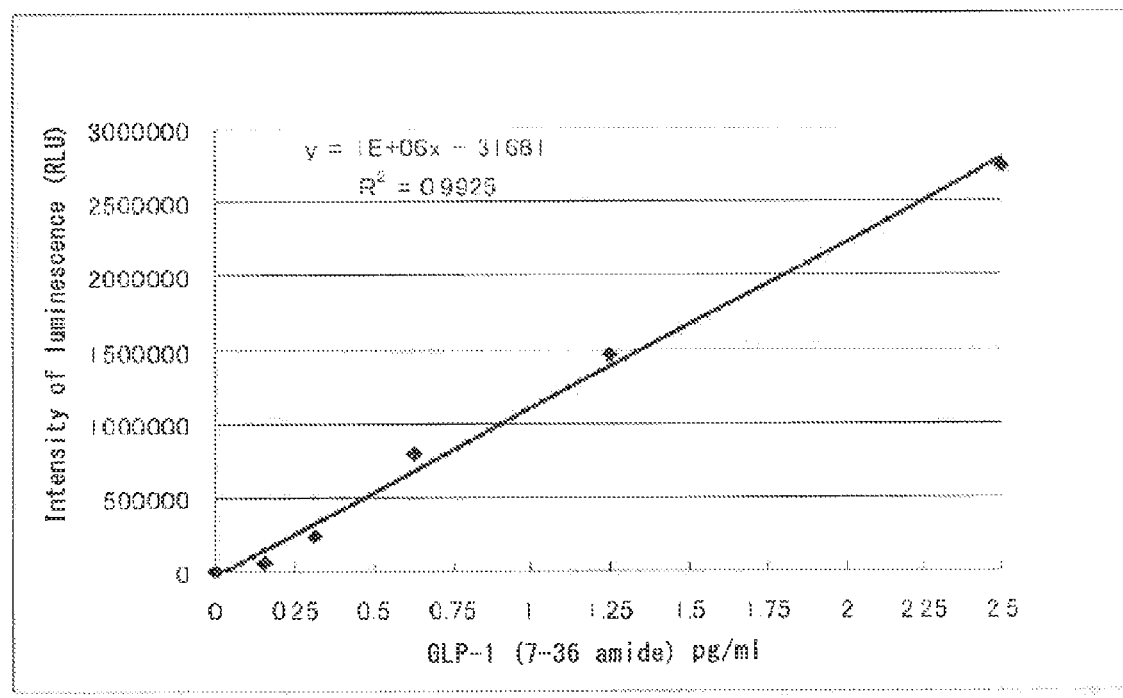
FIG. 22 shows that a kit provided by the present invention is capable of quantifying an active form of GLP-1.

As shown in FIG. 22, it was confirmed that the amount of luminescence was increased with linearity.

7. Sensitivity Comparison with Existing Kit Using GLP-1 Solution 1 ml ($3 \times 10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 µL of 4 mM ViviRen was added thereto. The mixture was seeded at 90 µL/well into a 96-well plate. The cells were cultured for 4 hours with an AVP solution diluted ½, ¼, ⅛, 1/16, or 1/32-fold with a sample buffer.

Values separately measured using the existing Millipore GLP-1 (Active)-ELISA kit (EGLP-35K) are also shown. The ELISA kit measures fluorescence intensity while the kit of the present invention measures chemiluminescence intensity. Thus, for comparison, a relative value (%) to the maximum amount of light (fluorescence or luminescence) emitted from each sample is shown. The kit of the present invention was confirmed to maintain linearity even at a dose of 1 pg/mL or lower and have excellent sensitivity, compared with the existing ELISA kit (see FIG. 23). The lowest detection sensitivity was 3.73 pg/ml for the existing ELISA kit and 0.078 pg/ml for the kit of the present invention.

Figure 23:
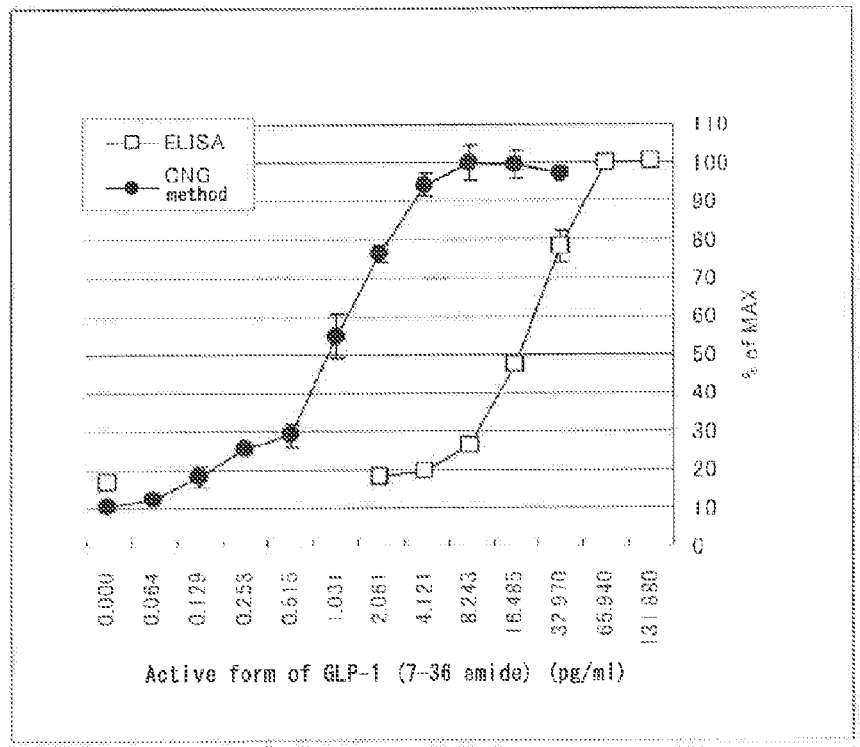
FIG. 23 shows the comparison of measurement ranges between a kit provided by the present invention and an existing kit for an active form of GLP-1 using EIA assay.

Moreover, it was demonstrated that the kit provided by the present invention can measure the active form of GLP-1 in a wider concentration range than that of the existing ELISA kit (see FIG. 23).

Figure 24:
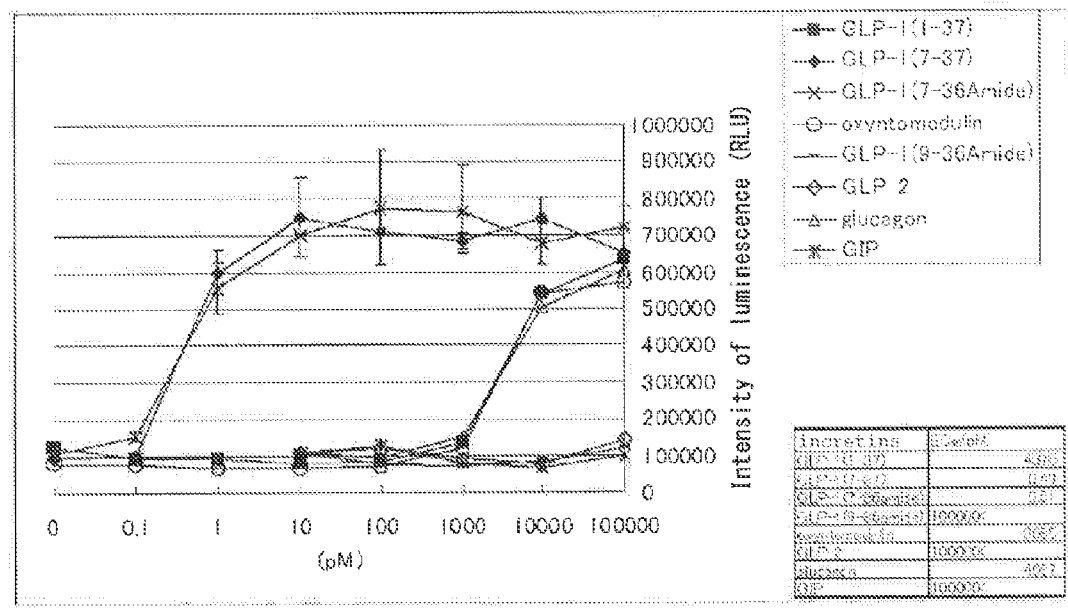
FIG. 24 shows study on the specificity of a kit provided by the present invention for an active form of GLP-1 among incretin-related peptides.

8. Study on Specificity of Kit Using GLP-1-Like Peptide 1 ml ($3\times10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 µL of 4 mM ViviRen was added thereto. The mixture was seeded at 90 µL/well into a 96-well plate. The cells were cultured for 3 hours with a GLP-1-like peptide solution diluted 1/10, 1/100, 1/1000, 1/10000, or $1/10^5$-fold with a sample buffer. The GLP-1-like peptide measurement sensitivity of the kit of the present invention is indicated by the EC50 value (pM) of each peptide (see FIG. 24). The kit exhibited reactivity for precursor GLP-1 (1-37), oxyntomodulin and glucagon, which are weak agonists against the GLP-1 receptor, at a concentration 10000 times higher compared with the active forms (GLP-1 (7-37) and GLP-1 (7-36 amide)) of GLP-1. Moreover, the kit hardly reacted with GLP-1 (9-36 amide), which is formed by the in vivo degradation of the active form of GLP-1, or GIP or GLP-2, which is incretin acting on other receptors, even at a concentration 1 million times higher compared with the active forms of GLP-1. It was demonstrated that the kit of the present invention is capable of assaying the active forms of GLP-1, i.e., GLP-1 (7-36 amide) and GLP-1 (7-37), with exceedingly high sensitivity and specificity.

Figure 25:
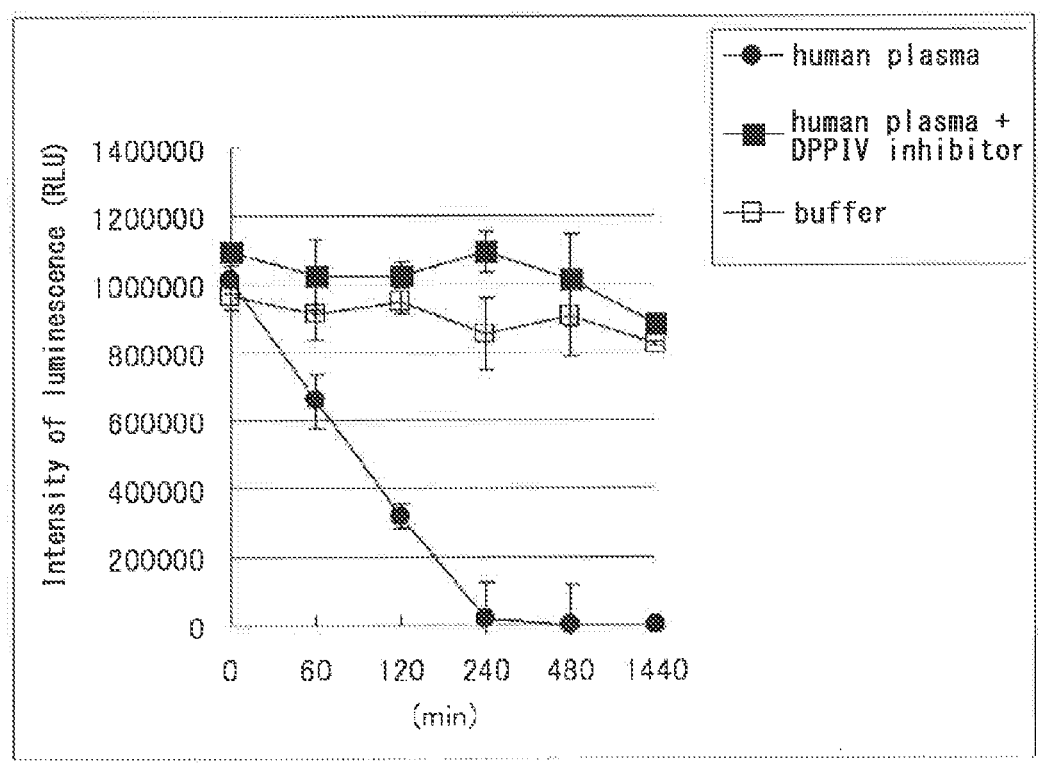
FIG. 25 shows the assay of the degradation of an active form of GLP-1 by DPP-IV enzyme in human plasma using a kit provided by the present invention.

9. Assay of Active Form of GLP-1 in Human Plasma 1 ml ($3\times10^6$ cells/ml) of the frozen cells prepared in 1 was thawed in a warm bath and suspended in 10 mL of a washing buffer. After centrifugation at 1000 rpm for 5 minutes, 12 mL of a culture buffer was added to the obtained precipitate, and 6 L of 4 mM ViviRen was added thereto. The mixture was seeded at 50 µL/well into a 96-well plate. GLP-1-containing samples prepared by adding the active form of GLP-1 (7-36 amide) at a final concentration of 16.5 pg/ml (5 µM) to normal individual plasma or a buffer solution were used. Millipore DPP-IV inhibitor (DPP44-010) was added at a concentration of 20 uL per m of plasma in order to inhibit the activity of DPP-IV peptidase in plasma. The mixture was added to the plate at 10 µL/well, and the cells were cultured for 4 hours. 100 mM $CaCl_2$ solution was added thereto at 50 L/well, and the amount of luminescence was measured using a luminometer. The results are shown in FIG. 25.

GLP-1 activity disappeared over time in human plasma compared with the buffer solution, and the disappearance was inhibited by the DPP-IV inhibitor. The degradation of GLP-1 by the activity of DPP-IV enzyme was able to be monitored using the kit of the present invention.

Figure 26:
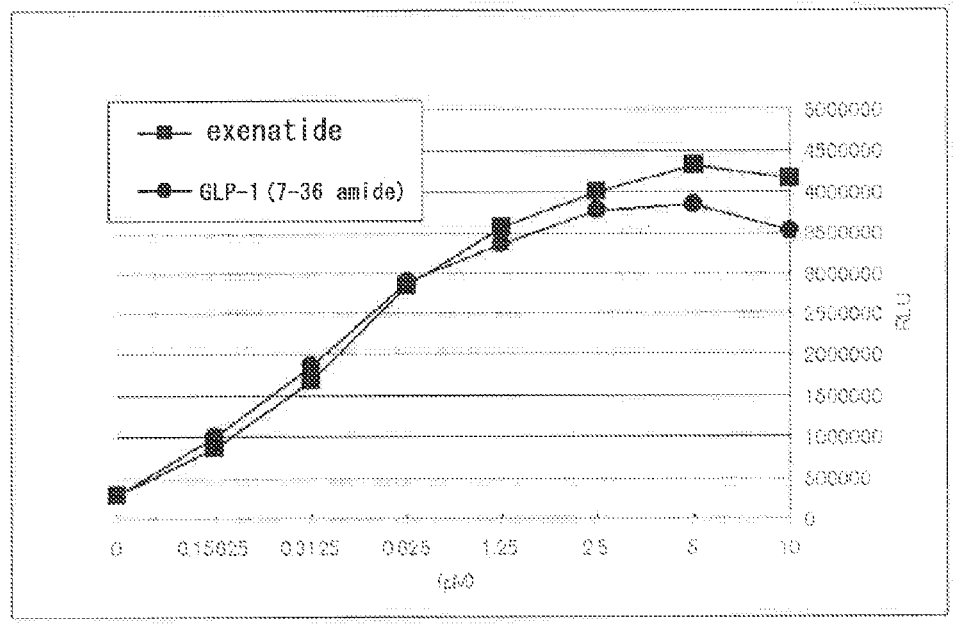
FIG. 26 shows concentrations of exenatide and GLP-1 and an amount of luminescence when a GLP-1 receptor agonist Byetta (exenatide), which is a therapeutic drug for diabetes mellitus, and an active form of GLP-1 (7-36 amide) were added to cell lines.

10. Detection of GLP-1 Agonist and GLP-1 Antagonist 1 ml ($3\times10^6$ cells/ml) of the frozen cells prepared in 1 was thawed in a warm bath and suspended in 10 mL of a washing buffer. The suspension was centrifuged at 1000 rpm for 5 minutes. 12 mL of a culture buffer was added to the obtained precipitate, and 6 µL of 4 mM ViviRen was added thereto. The mixture was seeded at 90 µL/well into a 96-well plate. Exenatide serially diluted with a calcium-containing culture buffer was added thereto, and the cells were cultured for 3 hours. 100 mM $CaCl_2$ solution was added thereto at 50 µL/well, and the amount of luminescence was measured using a luminometer (FIG. 26). Exenatide is a GLP-1-like peptide contained in the salivary gland of Gila monster lizard and has a long half-life because of its resistance to DPP-IV. Exenatide has already been launched as a therapeutic drug for type 2 diabetes mellitus. It was demonstrated that the kit of the present invention is capable of assaying not only natural GLP-1 but also an analog having GLP-1 receptor agonistic activity with high sensitivity.

Next, the activity of a GLP-1 antagonist was measured. 1 ml ($3\times10^6$ cells/ml) of the frozen cells prepared in 1 was thawed in a warm bath and suspended in 10 mL of a washing buffer. The suspension was centrifuged at 1000 rpm for 5 minutes. 12 mL of a culture buffer was added to the obtained precipitate, and 6 µL of 4 mM ViviRen was added thereto. The mixture was seeded at 90 µL/well into a 96-well plate.

Figure 27:
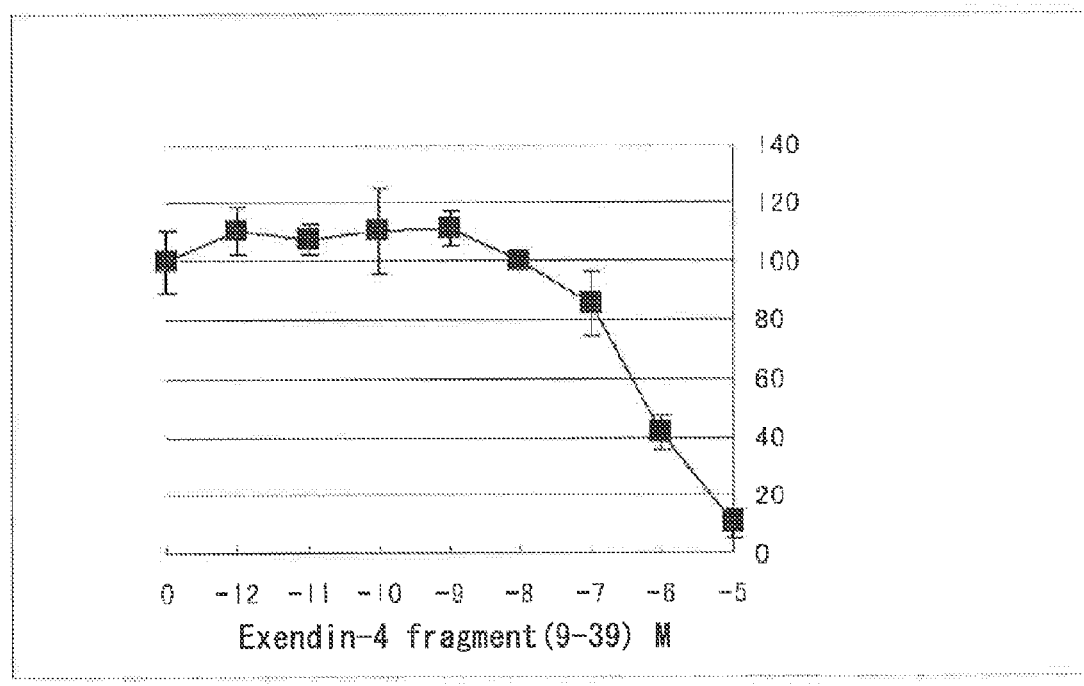
FIG. 27 shows a concentration of a GLP-1 receptor antagonist exendin fragment (9-39) and an amount of luminescence after culture of cells with the exendin fragment (9-39) and subsequent addition of 10 pM (final concentration) GLP-1 (7-36 amide).
Figure 28:
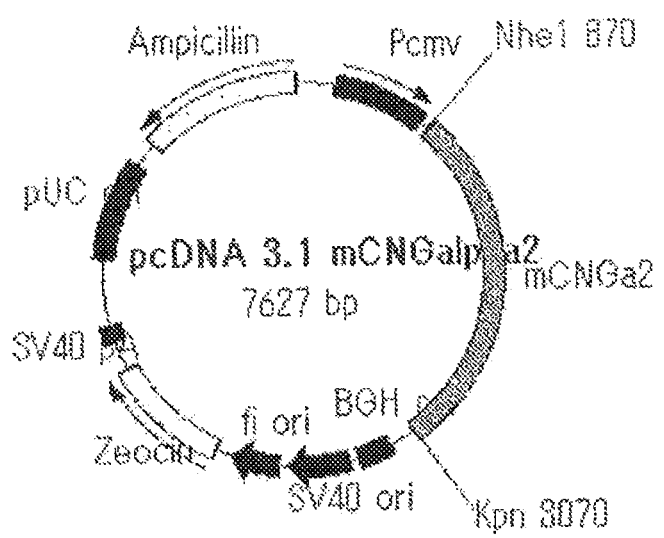
FIG. 28 shows a plasmid pmCNGα2.
Figure 29:
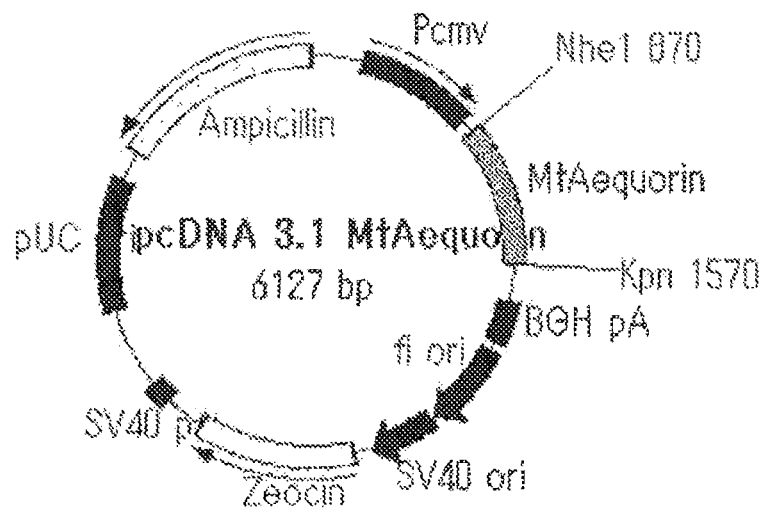
FIG. 29 shows a plasmid pcDNA mt sAEQ.

Exendin-4 (9-39) was added thereto at 10 µL/well, and the cells were cultured for 3 hours. $10^{-11}$ M GLP-1 was added thereto at 10 µL/well, and the amount of luminescence was measured using a luminometer. The GLP-1 antagonist exendin-4 (9-39) inhibited the agonistic action of added GLP-1 in a concentration dependent manner (FIG. 27).

INDUSTRIAL APPLICABILITY

The present invention can provide a method and a kit for measuring the amount of a physiologically active substance that binds to a receptor that alters intracellular cAMP concentration, which are easy to manipulate and are safe. Thus, a disease associated with the physiologically active substance can be diagnosed.

The invention claimed is:

1. A transformed cell, wherein the cell expresses Gs-coupled GPCR, wherein the GS-coupled GPCR is a GLP-1 receptor or a vasopressin V2 receptor,
a modified CNG calcium channel having the amino acid sequence represented by SEQ ID NO: 2, and
a modified apoaequorina having the amino acid sequence represented by SEQ ID NO: 3.

2. A kit for measuring the amount of an active form of GLP-1 or the amount of AVP in a biological sample, comprising a cell according to claim 1.

3. The kit according to claim 2, wherein the kit is for diagnosing diabetes insipidus or SIADH, for determining either a hypotonic or hypertonic fluid infusion to be selected or for determining the effect of a GLP-1-related therapeutic drug.

4. The kit according to claim 2, wherein the cell is a frozen cell.

5. The kit according to claim 2, further comprising a luminescent substrate for the calcium sensitive protein.

6. The kit according to claim 5, wherein the luminescent substrate for the calcium sensitive protein is coelenterazine or a coelenterazine derivative.

7. The kit according claim 2, wherein the kit comprises the transformed cell expressing:
a vasopressin V2 receptor,
a modified CNG calcium channel having the amino acid sequence represented by SEQ ID NO: 2, and
a modified apoaequorin having the amino acid sequence represented by SEQ ID NO: 3.

8. The kit according to claim 2, wherein the kit comprises the transformed cell expressing:
a GLP-1 receptor,
a modified CNG calcium channel having the amino acid sequence represented by SEQ ID NO: 2, and
a modified apoaequorin having the amino acid sequence represented by SEQ ID NO: 3.

9. The transformed cell according to claim 1, wherein the cell is a frozen cell.

10. The transformed cell according to claim 1, wherein the cell expresses a vasopressin V2 receptor.

11. The transformed cell according to claim 10, wherein the vasopressin V2 receptor has the amino acid sequence represented by SEQ ID NO: 1.

12. The transformed cell according to claim 1, wherein the cell expresses a GLP-1 receptor.

13. The transformed cell according to claim 12, wherein the GLP-1 receptor has the amino acid sequence represented by SEQ ID NO:8.

* * * * *